US012617831B2

(12) United States Patent
Mabilleau et al.

(10) Patent No.: US 12,617,831 B2
(45) Date of Patent: May 5, 2026

(54) PEPTIDE TARGETING GIP AND GLP-2 RECEPTORS FOR TREATING BONE DISORDERS

(71) Applicants:UNIVERSITE D'ANGERS, Angers (FR); CENTRE HOSPITALIER UNIVERSITAIRE D'ANGERS, Angers (FR)

(72) Inventors: Guillaume Mabilleau, Avrille (FR); Aleksandra Mieczkowska, Avrille (FR)

(73) Assignees: UNIVERSITE D'ANGERS, Angers (FR); CENTRE HOSPITALIER UNIVERSITAIRE D'ANGERS, Angers (FR)

( * ) Notice: Subject to any disclaimer, the term of this patent is extended or adjusted under 35 U.S.C. 154(b) by 740 days.

(21) Appl. No.: 17/431,598

(22) PCT Filed: Feb. 21, 2020

(86) PCT No.: PCT/EP2020/054604
§ 371 (c)(1),
(2) Date: Aug. 17, 2021

(87) PCT Pub. No.: WO2020/169792
PCT Pub. Date: Aug. 27, 2020

(65) Prior Publication Data
US 2022/0112261 A1 Apr. 14, 2022

(30) Foreign Application Priority Data

Feb. 21, 2019 (EP) .................................... 19305210

(51) Int. Cl.
| | |
|---|---|
| *A61K 38/00* | (2006.01) |
| *A61L 27/22* | (2006.01) |
| *A61L 27/54* | (2006.01) |
| *A61P 19/08* | (2006.01) |
| *C07K 14/575* | (2006.01) |
| *C07K 14/605* | (2006.01) |

(52) U.S. Cl.
CPC .......... *C07K 14/605* (2013.01); *A61L 27/227* (2013.01); *A61L 27/54* (2013.01); *A61P 19/08* (2018.01); *C07K 14/575* (2013.01); *A61K 38/00* (2013.01); *A61L 2300/252* (2013.01); *A61L 2300/412* (2013.01); *A61L 2400/06* (2013.01); *A61L 2430/02* (2013.01); *A61L 2430/24* (2013.01); *C07K 2319/50* (2013.01)

(58) Field of Classification Search
CPC .............. A61K 38/00; A61L 2300/252; A61L 2300/412; A61L 2400/06; A61L 2430/02; A61L 2430/24; A61L 27/227; A61L 27/54; A61P 19/08; C07K 14/575; C07K 14/605; C07K 2319/50
See application file for complete search history.

(56) References Cited

U.S. PATENT DOCUMENTS

| | | | |
|---|---|---|---|
| 6,410,508 | B1 | 6/2002 | Isales |
| 2002/0037836 | A1 | 3/2002 | Henriksen |
| 2007/0135345 | A1 | 6/2007 | Henriksen et al. |

FOREIGN PATENT DOCUMENTS

| | | | | |
|---|---|---|---|---|
| JP | 2002526554 A | 8/2002 | | |
| JP | 2004508410 A | 3/2004 | | |
| JP | 2016169171 A | 9/2016 | | |
| WO | 00/20592 | 4/2000 | | |
| WO | 2018/069442 | 4/2018 | | |
| WO | WO-2018069442 A1 * | 4/2018 | .............. | A61P 19/08 |
| WO | 2019/072963 | 4/2019 | | |

OTHER PUBLICATIONS

Dacambra et al. (Biochemistry 2000, 39: 8888-8894). Structural Determinants for Activity of Glucagon-like Peptide-2 (Year: 2000).*
Wiśniewski et al., "Synthesis and Pharmacological Characterization of Novel Glucagon-like Peptide-2 (GLP-2) Analogues with Low Systemic Clearance", Journal of Medicinal Chemistry, 2016, vol. 59, pp. 3129-3139.
International Search Report for PCT/EP2020/054604 dated Mar. 16, 2020, 4 pages.
Written Opinion of the ISA for PCT/EP2020/054604 dated Mar. 16, 2020, 6 pages.

* cited by examiner

*Primary Examiner* — Lianko G Garyu
*Assistant Examiner* — Mercy H Sabila
(74) *Attorney, Agent, or Firm* — NIXON & VANDERHYE

(57) ABSTRACT

Disclosed is an isolated peptide including the consensus amino acid sequence SEQ ID NO: 1:

```
                                        (SEQ ID NO: 1)
HGEGSFX7SDX10 SX12X13LDKLAARDFVNWLLQTK
``` wherein X7 is any amino acid residue, X10 is any amino acid residue, X12 is any amino acid residue and X13 is any amino acid residue. Also disclosed are methods of using such peptide in the treatment of bone disorders.

14 Claims, 24 Drawing Sheets

Specification includes a Sequence Listing.

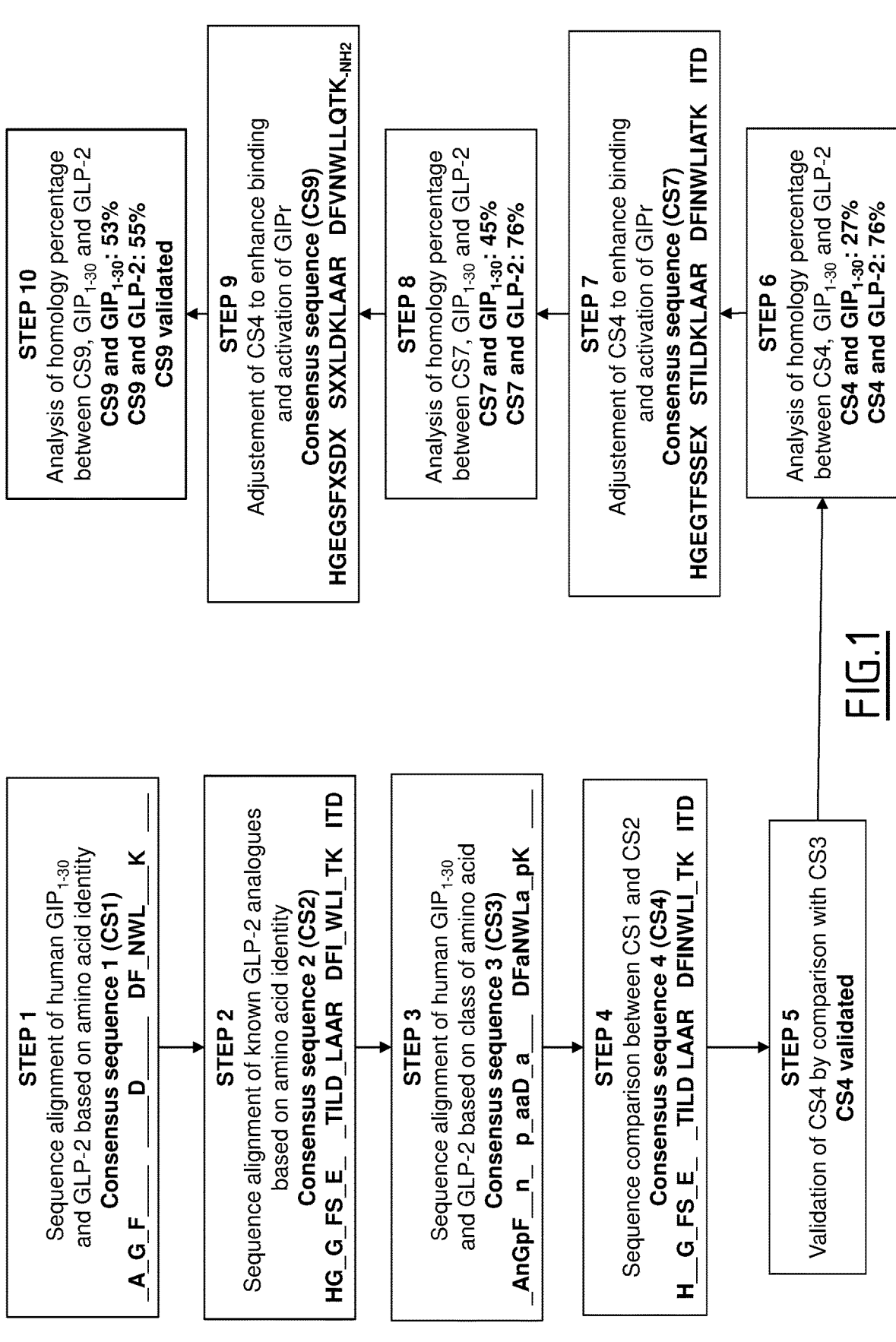

STEP 10
Analysis of homology percentage between CS9, GIP$_{1-30}$ and GLP-2 based on amino acid identity
CS9 and GIP$_{1-30}$: 53%
CS9 and GLP-2: 55%
CS9 validated

STEP 9
Adjustement of CS4 to enhance binding and activation of GIPr
Consensus sequence (CS9)
HGEGSFXSDX SXXLDKLAAR DFVNWLLQTK$_{-NH2}$

STEP 8
Analysis of homology percentage between CS7, GIP$_{1-30}$ and GLP-2
CS7 and GIP$_{1-30}$: 45%
CS7 and GLP-2: 76%

STEP 7
Adjustement of CS4 to enhance binding and activation of GIPr
Consensus sequence (CS7)
HGEGTFSSEX STILDKLAAR DFINWLIATK ITD

STEP 6
Analysis of homology percentage between CS4, GIP$_{1-30}$ and GLP-2
CS4 and GIP$_{1-30}$: 27%
CS4 and GLP-2: 76%

STEP 1
Sequence alignment of human GIP$_{1-30}$ and GLP-2 based on amino acid identity
Consensus sequence 1 (CS1)
A_G_F___D___DF_NWL__K___

STEP 2
Sequence alignment of known GLP-2 analogues based on amino acid identity
Consensus sequence 2 (CS2)
HG_G_FS_E__TILD_LAAR_DFI_WLI_TK_ITD

STEP 3
Sequence alignment of human GIP$_{1-30}$ and GLP-2 based on class of amino acid
Consensus sequence 3 (CS3)
_AnGpF__n__p_aaD_a___DFaNWLa_pK___

STEP 4
Sequence comparison between CS1 and CS2
Consensus sequence 4 (CS4)
H__G_FS_E__TILD_LAAR_DFINWLI_TK_ITD

STEP 5
Validation of CS4 by comparison with CS3
CS4 validated

FIG.1

Peptide Co-3

GL-0001

```
HGEGSFGSDMSIALDKLAARDFVNWLLQTKITD
|::||:|  |:||  ||:|:||:|:||||||
HADGTFISDYSTILDNLAARDFINWLIQTKITD
```

```
HGEGSFGSDFSIALDKLAARDFVNWLLQTK---
|:::||||||:|:|||:|||:|||:|||
HADGTFISDYSTILDNLAARDFINWLIQTKITD
```

GL-0007

Peptide Co-7

```
HGEGSFGSDMSIALDKLAARDFVNWLLQTKITD
|:::|:|  ||:|:|:||:||:|:|||||
HAEGTFISDYSIAMDKLAARDFINWLIQTKITD
```

```
HGEGSFGSDFSIALDKLAARDFVNWLLQTK---
|:::|:|  ||:|:|:||:|||:|||:|||
HAEGTFISDYSIAMDKLAARDFINWLIQTKITD
```

Peptide Co-19

```
HGEGSFGSDMSIALDKLAARDFVNWLLQTKITD
|::|:*|  ||:|  ||:|:||:|:||||||
HADGTFISDYSTILDNLAARDFINWLIQTKGKK
```

```
HGEGSFGSDFSIALDKLAARDFVNWLLQT---K
|:::|  ||:|  ||:|:||:|:||:|||:||||
HADGTFISDYSTILDNLAARDFINWLIQTKGKK
```

FIG.19

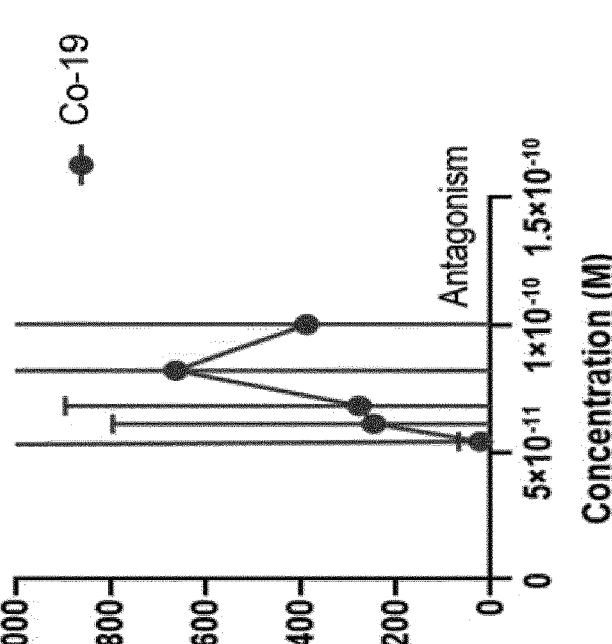
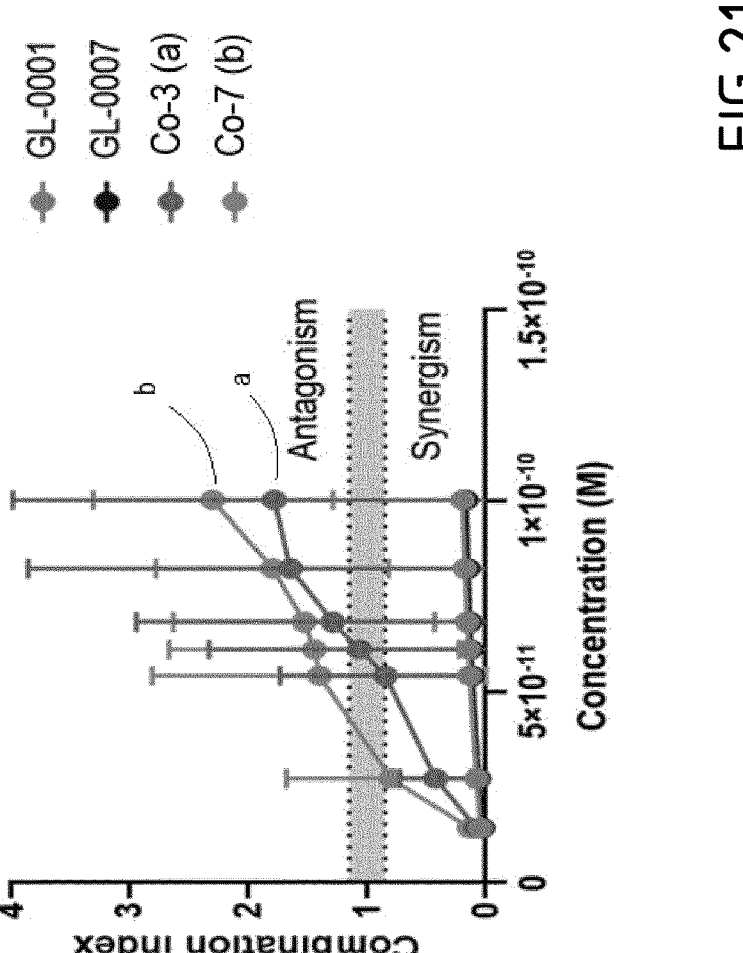
FIG.21

1

PEPTIDE TARGETING GIP AND GLP-2 RECEPTORS FOR TREATING BONE DISORDERS

BACKGROUND OF THE INVENTION

Field of the Invention

The present invention concerns the treatment of bone disorders.

Description of the Related Art

Today, bone fragilities represent an important public health issue. Indeed, with the population ageing, the number of bone fractures is constantly increasing (377 000 fractures in France in 2013) with serious socio-economical consequences.

Bone tissue is a tissue which is permanently remodeled in order to adapt to mechanical stress (gravity, movements, etc.) but also to metabolic stress (release or storage of calcium, phosphate, proteins, etc.) and represents a system balanced between bone formation and bone resorption. Bone remodeling depends on several factors such as calcium phosphate metabolism hormones, mechanical load or local factors.

Bone fragilities happen when an imbalance of bone formation and bone resorption activities, during bone remodeling, occurs, or when bone cells activity is disturbed. This leads either to a decrease in the amount of bone tissue or to an alteration of the bone matrix quality, or to both of them, and results in an increased bone fragility and a high risk of fracture.

Several therapeutic solutions to treat bone fragilities exist (vitamin D, bisphosphonates, anti-RANKL, recombinant calcitonin, intermittent injection of recombinant parathormone, modulators of estrogens receptor) or are about to be marketed (anti-cathepsin K, anti-sclerostin, PTHrP analog). However, these molecules display use restrictions and cannot be administered to all the patients suffering from bone fragility. Additionally, some of these molecules have side effects (mandibular osteonecrosis, atypical fracture of the femur, risk of cancer), which demand strict monitoring and regular follow-up of the patients. Furthermore, the efficiency of these molecules remains moderate, and despite their use, it is estimated that only 50% of bone fragility fractures are prevented in case of ongoing treatment, confirming the need to find new therapeutic pathways.

SUMMARY OF THE INVENTION

The present invention meets this need.

It was recently shown that intestinal hormones, released after the entry of the food bowl in the intestine, acted on bone remodeling.

Among the plethora of bioactive peptides that the gastrointestinal tract secretes, a class of peptides called incretins has emerged as important modulators of energy metabolism. Incretins are hormones that are secreted from the intestine in response to glucose and stimulate insulin release in a glucose-dependent manner. Although several hormones with insulinotropic action are secreted by the gut, glucose-dependent insulinotropic polypeptide (GIP) and glucagon-like peptide-1 (GLP-1) are the only two physiological incretins identified so far. Recently, based on knockout preclinical animal models, potential beneficial effects of both GIP and GLP-1 have been highlighted on diabetes-induced bone fragility.

The present invention arises from the unexpected finding by the inventors that a peptide bearing a specifically designed consensus sequence was capable to bind to and activate both glucose-dependent insulinotropic polypeptide (GIP) receptor and glucagon-like peptide 2 (GLP-2) receptor similarly to respective GIP and GLP-2 native peptides, and thereby to control bone remodeling. In particular, the inventors show that this dual-target peptide increased enzymatic cross-linking of collagen matrix produced by osteoblasts at a higher level than each native peptide and reduced the number of generated osteoclasts in a more important way than each native peptide.

The present invention thus concerns an isolated peptide comprising the consensus amino acid sequence SEQ ID NO: 1:

$$\text{(SEQ ID NO: 1)}$$
$$\text{HGEGSFX}_7\text{SDX}_{10}\ \text{SX}_{12}\text{X}_{13}\text{LDKLAARDFVNWLLQTK}$$

wherein $X_7$ is any amino acid residue, $X_{10}$ is any amino acid residue, $X_{12}$ is any amino acid residue and $X_{13}$ is any amino acid residue.

The present invention also concerns a pharmaceutical composition comprising a peptide of the invention.

The present invention further concerns an implantable medical device comprising, in particular coated with, the peptide of the invention.

Another object of the invention is the in vitro use of a peptide of the invention for coating an implantable medical device.

A further object of the invention concerns a peptide of the invention or a pharmaceutical composition of the invention for use in a method for treating and/or preventing a bone disorder in a subject.

In a particular embodiment, said bone disorder is a manifestation, in bones, of a metabolic or hormonal disorder.

The present invention also concerns a bone filling biomaterial comprising the peptide of the invention.

The present invention further concerns a bone filling biomaterial comprising the peptide of the invention for use for bone regeneration.

DESCRIPTION OF THE PREFERRED EMBODIMENTS

Definitions

In the context of the invention, the term "peptide" refers to native peptides (either proteolysis products or synthetically synthesized peptides) and further to peptidomimetics, such as peptoids and semipeptoids which are peptide analogs, which may have, for example, modifications rendering the peptides more stable while in a body, or more immunogenic. Such modifications include, but are not limited to, cyclization, N-terminus modification, C-terminus modification, acylation, PEGylation, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, CA. Ramsden Gd., Chapter 17.2, F. Choplin Pergamon Press (1992).

The peptides of the invention preferably consist of at least 30 amino acids, at least 31 amino acids, at least 32 amino acids or at least 33 amino acids, and preferably less than 50 amino acids. In a particular embodiment, the peptides of the invention further comprise, in addition to the at least 30, 31, 32 or 33 amino acids, a peptide tag as defined below.

As used herein, the term "amino acid" is understood to include: the 20 naturally occurring amino acids i.e. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; amino acids harbouring the post-translational modifications which can be found in vivo such as hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

By "non polar amino acid" is meant herein a class of amino acids in which the variable R-group is comprised of mostly hydrocarbons. Non polar amino acids include glycine, alanine, proline, valine, leucine, isoleucine, methionine, tryptophan and phenylalanine.

As used herein, the term isolated peptide' refers to any peptide, irrespective of its method of synthesis, which is locationally distinct from the naturally occurring protein sequence of which it may form a part in nature.

Peptide

As indicated above and shown in the examples below, the inventors designed a specifically consensus amino acid sequence, so that the peptide bearing this sequence was capable to bind to and activate both glucose-dependent insulinotropic polypeptide (GIP) receptor and glucagon-like peptide 2 (GLP-2) receptor similarly to respective GIP and GLP-2 native peptides.

Accordingly, the present invention concerns an isolated peptide comprising or consisting of the consensus amino acid sequence SEQ ID NO: 1:

(SEQ ID NO: 1)
HGEGSFX$_7$SDX$_{10}$SX$_{12}$X$_{13}$LDKLAARDFVNWLLQTK wherein X, is any amino acid residue, X$_{10}$ is any amino acid residue, X$_{12}$ is any amino acid residue and X$_{13}$ is any amino acid residue.

In a particular embodiment, X$_7$ is an amino acid selected from the group consisting in glycine, valine, threonine and serine, preferably from the group consisting in glycine, valine and threonine.

In another particular embodiment, X$_{10}$ is an amino acid selected from the group consisting in methionine, leucine and phenylalanine.

In another particular embodiment, X$_{12}$ is an amino acid selected from the group consisting in isoleucine, valine and threonine, preferably from the group consisting in isoleucine and valine.

In another particular embodiment, X$_{13}$ is a non polar amino acid, preferably an amino acid selected from the group consisting in alanine, valine and isoleucine, in particular from the group consisting in alanine and valine.

In a particular embodiment, X$_7$ is an amino acid selected from the group consisting in glycine, valine, threonine and serine, X$_{10}$ is an amino acid selected from the group consisting in methionine, leucine and phenylalanine, X$_{12}$ is an amino acid selected from the group consisting in isoleucine, valine and threonine, and X$_{13}$ is a non polar amino acid.

In another particular embodiment, X$_7$ is an amino acid selected from the group consisting in glycine, valine, threonine and serine, X$_{10}$ is an amino acid selected from the group consisting in methionine, leucine and phenylalanine, X$_{12}$ is an amino acid selected from the group consisting in isoleucine, valine and threonine, and X$_{13}$ is an amino acid selected from the group consisting in alanine, valine and isoleucine.

In another particular embodiment, X$_7$ is an amino acid selected from the group consisting in glycine, valine and threonine, X$_{10}$ is an amino acid selected from the group consisting in methionine, leucine and phenylalanine, X$_{12}$ is an amino acid selected from the group consisting in isoleucine and valine, and X$_{13}$ is an amino acid selected from the group consisting in alanine and valine.

In a preferred embodiment, the C-terminal lysine of the peptide of the invention is amidated.

In a particular embodiment, the peptide of the invention comprises or consists of the consensus amino acid sequence SEQ ID NO: 2:

(SEQ ID NO: 2)
HGEGSFX$_7$SDX$_{10}$ SX$_{12}$X$_{13}$LDKLAARDFVNWLLQTKITD wherein X$_7$, X$_{10}$, X$_{12}$ and X$_{13}$ are as defined above.

In a particular embodiment, in the peptide of the invention, K$_{16}$ and/or K$_{30}$ further bear a modification, typically a post-translational modification. In a more particular embodiment, in the peptide of the invention, K$_{16}$ and/or K$_{30}$ is acylated or PEGylated.

The peptide according to the invention may further comprise a peptide tag at its N-terminal or C-terminal end, in particular at its C-terminal end.

Any of a variety of art recognized peptide tags can be employed in the present invention. For example, suitable peptide tags include a: FLAG peptide, short FLAG peptide, His-6 peptide, Glutathion-S-Transferase (GST), Staphylococcal protein A, Streptococcal protein G, Calmodulin, Calmodulin binding peptides, Thioredoxin, β-galactosidase, Ubiquitin, Chloramphenicol cetyltransferasel S-peptide (Ribonuclease A, residues 1-20), Myosin heavy chain, DsbA, Biotin subunit, Avidin, Streptavidin, Sfrp-tag, c-Myc, Dihydrofolate reductase, CKS, Polyarginine, Polycisteine, Polyphenylalanine, lac Repressor, N-terminus of the growth hormone, Maltose binding protein, Galactose binding protein, Cyclomaltodextrin glucanotransferase, Callulose binding domain, Haemolysin A, TφE or TφLE, Protein kinase sites, BAI epitope, Btag, VP7 region of Bluetongue virus, Green Fluorescent Protein or any fluorochromes.

The peptide tag can include one or more specific protease cleavage sites.

In a preferred embodiment, the peptide tag is a peptide consisting of the sequence GAADDDDD (SEQ ID NO: 13).

In a particular embodiment, the peptide of the invention is selected from the group consisting in the peptides:

GL-0001 of sequence
(SEQ ID NO: 3)
HGEGSFGSDMSIALDKLAARDFVNWLLQTKITD

GL-0007 of sequence
(SEQ ID NO: 4)
HGEGSFGSDFSIALDKLAARDFVNWLLQTK-NH$_2$

5

-continued
```
GL-0001-Tag of sequence
                              (SEQ ID NO: 5)
HGEGSFGSDMSIALDKLAARDFVNWLLQTKITDGAADDDDDD GL-0002 of sequence
                              (SEQ ID NO: 6)
HGEGSFVSDMSIVLDKLAARDFVNWLLQTK-NH2

GL-0003 of sequence
                              (SEQ ID NO: 7)
HGEGSFVSEMSIVLDKLAARDFVNWLLQTK-NH2

GL-0004 of sequence
                              (SEQ ID NO: 8)
HGEGSFVSDMSVVLDKLAARDFVNWLLQTK-NH2

GL-0005 of sequence
                              (SEQ ID NO: 9)
HGEGSFVSDLSVVLDKLAARDFVNWLLQTK-NH2

GL-0006 of sequence
                              (SEQ ID NO: 10)
HGEGSFVSDFSVVLDKLAARDFVNWLLQTK-NH2

GL-0008 of sequence
                              (SEQ ID NO: 11)
HGEGSFTSDFSIALDKLAARDFVNWLLQTK-NH2,
and GL-0009 of sequence
                              (SEQ ID NO: 12)
HGEGSFVSDFSIALDKLAARDFVNWLLQTK-NH2 .
```

In a preferred embodiment, the peptide of the invention is selected from the group consisting in the peptides:

```
GL-0001 of sequence
                              (SEQ ID NO: 3)
HGEGSFGSDMSIALDKLAARDFVNWLLQTKITD
and GL-0007 of sequence
                              (SEQ ID NO: 4)
HGEGSFGSDFSIALDKLAARDFVNWLLQTK-NH2 .
```

In a particular embodiment, the peptide of the invention is the peptide GL-0001 of sequence HGEGSFGSDM-SIALDKLAARDFVNWLLQTKITD (SEQ ID NO: 3).

In particular embodiments, the peptide of the invention is modified so that its stability, in particular in vivo, and/or its circulation time is increased, compared to non-modified peptides. Potential modifications that may be performed include those defined in the section "Peptide" above such as PEGylation, acylation, biotinylation, acetylation, formylation, ubiquitination, amidation, enzyme labeling, or radio-labeling. For instance, varying degrees of PEGylation may be used to vary the half-life of the peptide, with increased PEGylation corresponding to increased half-life. Modifications may occur at any location on the peptide, including the peptide backbone, the amino acid side chains, and the amino or carboxy termini.

In an embodiment, the peptide of the invention can be modified by addition of a TAT (trans-activating transcriptional activator) peptide, a well-known peptide commonly used for the delivery of peptides and known to facilitate the in vivo administration of short peptides.

In another embodiment, the peptide of the invention may be modified by addition of the Fc domain of an antibody. The Fc domain of an antibody is a relatively constant region that is responsible for biological activity rather than antigen binding. A variety of therapeutic polypeptides have been created using the Fc domain to increase the half-life of the polypeptide or to incorporate certain biological functions such as the ability to bind to a particular receptor. Attachment of an Fc domain to the peptide of the present invention is likely to increase the half-life of the peptide. The Fc domain may comprise portions of a digested, naturally occurring antibody, or it may be derived from a recombinant or humanized antibody.

The peptides of the invention are capable of activating both GIP and GLP-2 receptors.

By "GIP" or "glucose-dependent insulinotropic polypeptide" is meant herein an inhibiting hormone of the secretin family of hormones, which belongs to the class of incretins, and which stimulates insulin secretion. It is derived from a 153-amino acid proprotein encoded, in humans, by the GIP gene and circulates as a biologically active 42-amino acid peptide. It is synthesized by K cells, which are found in the mucosa of the duodenum and the jejunum of the gastrointestinal tract.

By "GIP receptor" or "GIP-R" is meant herein a protein encoded, in humans, by the GIPR gene, which is a member of the 7-transmembrane protein family, a class of G protein-coupled receptors, found on beta-cells in the pancreas.

By "activation of the GIP receptor", it is meant herein that binding of the peptide to the GIP-R results in activation of intracellular signaling pathways, such as but not restricted to, increase in cyclic adenosine monophosphate (cAMP).

Activation of the GIP receptor can be detected by any technique well-known from the skilled person. In particular, activation of the GIP receptor can be detected by evaluating cAMP by biochemical and/or imaging assays such as but not restricted to enzyme linked immunosorbent assay or Forster resonance energy transfer (FRET).

By "GLP-2" or "glucagon-like peptide 2" is meant herein a 33 amino acid peptide created by specific post-translational proteolytic cleavage of proglucagon in a process that also liberates the related glucagon-like peptide-1. GLP-2 is produced by the intestinal endocrine L cells and by various neurons in the central nervous system.

By "GLP-2 receptor" or "GLP-2R" is meant a protein encoded, in humans, by the GLP2R gene, which is member of the G protein-coupled receptor family closely related to the GLP1 receptor.

By "activation of the GLP-2 receptor", it is meant herein that binding of the peptide to the GLP2-R results in activation of intracellular signaling pathway, such as but not restricted to, increase in cAMP.

Activation of the GLP-2 receptor can be detected by any technique well-known from the skilled person. In particular, activation of the GLP-2 receptor can be detected by evaluating cAMP by biochemical and/or imaging assays such as but not restricted to enzyme linked immunosorbent assay or Forster resonance energy transfer (FRET).

Pharmaceutical Composition and Medical Device

The present invention also concerns a pharmaceutical composition comprising a peptide as defined the section "Peptide" above, and optionally a pharmaceutically acceptable excipient.

The term "pharmaceutically acceptable" refers to properties and/or substances which are acceptable for administration to a subject from a pharmacological or toxicological point of view. Further "pharmaceutically acceptable" refers to factors such as formulation, stability, patient acceptance and bioavailability which will be known to a manufacturing pharmaceutical chemist from a physical/chemical point of view.

As used herein, "pharmaceutically acceptable excipient" refers to any substance in a pharmaceutical composition different from the active ingredient. Said excipients can be liquids, sterile, as for example water and oils, including those of origin in the petrol, animal, vegetable or synthetic, as peanut oil, soy oil, mineral oil, sesame oil, and similar, disintegrate, wetting agents, solubilizing agents, antioxidant, antimicrobial agents, isotonic agents, stabilizing agents or diluents. Suitable adjuvants and/or pharmaceutical carriers are described in "Remington's Pharmaceutical Sciences" by E. W. Martin.

The pharmaceutical compositions of the invention can be formulated for a parenteral, e.g., intravenous, intradermal, intracerebroventricular, subcutaneous, intramuscular, intraperitoneal, oral (e.g., buccal, inhalation, nasal and pulmonary spray), intradermal, transdermal (topical), transmucosal or intraocular administration.

The peptide of the invention is particularly useful when used with an implantable medical device because it enables, among others, increasing and improving their integration in bones.

The present invention thus also concerns an implantable medical device comprising, in particular coated with, the peptide of the invention.

As used herein, an "implantable medical device" refers to any type of appliance that is totally or partly introduced, surgically or medically, into a subject's body or by medical intervention into a natural orifice, and which is intended to remain there after the procedure. The duration of implantation may be essentially permanent, i.e. intended to remain in place for the remaining lifespan of the subject; until the device biodegrades; or until it is physically removed. Examples of implantable medical devices include orthopaedic prostheses and dental implants.

The present invention further concerns the in vitro use of a peptide of the invention for coating an implantable medical device, as defined above.

Medical Indications

The inventors demonstrated that the peptides of the invention increased enzymatic cross-linking of collagen matrix produced by osteoblasts at a higher level than GIP and GLP-2 respectively and reduced the number of generated osteoclasts in a more important way than GIP and GLP-2. Accordingly, the peptide of the invention is particularly interesting to treat bone disorders.

The present invention thus also relates to a peptide as defined in the section "Peptide" above or a pharmaceutical composition as defined in the section "Pharmaceutical composition" above for use in a method for treating and/or preventing a bone disorder in a subject.

The present invention also concerns the use of a peptide as defined in the section "Peptide" above or of a pharmaceutical composition as defined in the section "Pharmaceutical composition" above for the manufacture of a medicament intended to treat and/or prevent a bone disorder.

The present invention also concerns a method for treating and/or preventing a bone disorder in a subject, comprising administering to a subject in need thereof a therapeutically effective amount of a peptide as defined in the section "Peptide" above or a pharmaceutical composition as defined in the section "Pharmaceutical composition" above.

By "bone disorder", it meant herein a disorder wherein bone formation, deposition, or resorption is abnormal. Bone disorders include, but are not limited to, any kind of primary or secondary osteoporosis (post-menopausal, glucocorticoid-induced, immobilization-induced, senile), osteopenia, diabetic bone disease, osteomalacia and rickets, bone dystrophies such as Paget's disease of bone, hypercalcemia of malignancy, osteopenia due to bone metastasis, osteosarcoma, Ewing tumour of bone, osteochondroma, bone abnormalities caused by cancer treatment, osteogenesis imperfecta, osteomyelitis, achondroplasia, avascular necrosis, osteopetrosis, myositis ossificans, periodontal disease, hyperparathyroidism, periarticular erosions in rheumatoid arthritis, bone erosions in ankylosing spondylitis and bone loss in anorexia nervosa.

Accordingly, in a particular embodiment, said bone disorder is selected from primary or secondary osteoporosis, (including post-menopausal, glucocorticoid-induced, immobilization-induced and senile osteoporosis), osteopenia, diabetic bone disease, osteomalacia and rickets, bone dystrophies such as Paget's disease of bone, hypercalcemia of malignancy, osteopenia due to bone metastasis, osteosarcoma, Ewing tumour of bone, osteochondroma, bone abnormalities caused by cancer treatment, osteogenesis imperfecta, osteomyelitis, achondroplasia, avascular necrosis, osteopetrosis, myositis ossificans, periodontal disease, hyperparathyroidism, periarticular erosions in rheumatoid arthritis, bone erosions in ankylosing spondylitis and bone loss in anorexia nervosa.

In a more particular embodiment, said bone disorder is osteogenesis imperfecta.

In a particular embodiment, said bone disorder is a manifestation, in bones, of a metabolic or hormonal disorder.

By "metabolic disorder" or "metabolic disease" is meant herein any disorder or disease induced by abnormal chemical reactions in the body that alter the normal metabolic process. Metabolic disorders include acid-base imbalance, metabolic brain diseases, disorders of calcium metabolism, DNA repair-deficiency disorders, glucose metabolism disorders, hyperlactatemia, iron metabolism disorders, lipid metabolism disorders, malabsorption syndromes, metabolic syndrome X, inborn error of metabolism, mitochondrial diseases, phosphorus metabolism disorders, porphyrias, proteostasis deficiencies, metabolic skin diseases, wasting syndrome and water-electrolyte imbalance.

Preferably, the metabolic disorder is selected from the group consisting in disorders of calcium metabolism, glucose metabolism disorders and phosphorus metabolism disorders.

By "hormonal disorder" or "hormonal disease" is meant herein a condition, disorder, or disease that occurs in a mammal due to overproduction and/or underproduction of any soluble molecule that acts at distance of its site of production by circulating in the blood stream, and is associated with, or related to, serum concentrations of insulin, glucagon, estrogen, testosterone, and/or sex hormone-binding globulin, thyroid hormones, parathyroid hormone, calcitonin, fibroblast-growth factor 23, calcitriol, that are below or above that of a young healthy disease-free mammal. Hormonal disorders include glucose homeostasis disorders, such as diabetes, hypoglycemia and glucagonoma; thyroid disorders such as goitre, hyperthyroidism, hypothyroidism, thyroiditis, and thyroid hormone resistance; calcium homeostasis disorders and metabolic bone diseases such as parathyroid gland disorders, osteoporosis, osteitis deformans, rickets and osteomalacia; pituitary gland disorders such as diabetes insipidus and hypopituitarism.

Preferably, the hormonal disorder is selected from the group consisting in diabetes, hyperthyroidism, hypothyroidism, thyroiditis, thyroid hormone resistance, calcium homeostasis disorders, parathyroid gland disorders, osteoporosis, osteitis deformans, rickets and osteomalacia.

The peptide of the invention is particularly useful when used with a bone filling biomaterial because it enables, among others, increasing and improving its integration in bones.

The present invention thus also concerns a bone filling biomaterial comprising the peptide of the invention.

By "bone filling biomaterial" is meant herein a biomaterial which can fill a bone defect in an initial stage (for example, liquid or paste) and is cured (for example, solidified or semi-solidified) with the lapse of time. Then, the "bone filling material" is a material which enables filling of bone defects (also including bone ameliorating such as osteosynthesis promotion and augmentation, in addition to osteosynthesis) to be performed on the bone at which the material is placed by way of fusion, absorption, substitution, organization, or the like.

The present invention further concerns a bone filling biomaterial comprising the peptide of the invention for use for bone regeneration.

In a particular embodiment, said bone filling biomaterial is for use in, but not restricted to, neurosurgery, orthopedic surgery or socket/bone defect filling.

In a particular embodiment, said peptide of the invention improves bone integration of said bone filling material, when used for bone regeneration.

By "subject" is meant herein a mammal, such as a rodent, a feline, a canine, or a primate. Preferably, a subject according to the invention is a human.

In a particular embodiment, the subject has an implantable medical device such as a prosthesis.

In the context of the invention, the term "treating" or "treatment" means reversing, alleviating, inhibiting the progress of the disorder or condition to which such term applies, or one or more symptoms of such disorder or condition.

In the context of the invention, the term "preventing" or "prevention" refers to the prophylactic treatment of a subject who is at risk of developing a condition resulting in a decrease in the probability that the subject will develop the condition or a delay in the development of the condition.

By a "therapeutically effective amount" of a peptide or a pharmaceutical composition of the invention is meant a sufficient amount of the peptide or composition to treat or prevent a specific disease, at a reasonable benefit/risk ratio applicable to any medical treatment. It will be understood, however, that the total daily usage of the peptide or composition of the present invention will be decided by the attending physician within the scope of sound medical judgment. The specific therapeutically effective dose level for any particular subject will depend upon a variety of factors including the disorder being treated and the severity of the disorder, activity of the specific peptides or compositions employed, the specific combinations employed, the age, body weight, general health, sex and diet of the subject, the time of administration, route of administration and rate of excretion of the specific peptides employed, the duration of the treatment, drugs used in combination or coincidental with the specific peptides employed, and like factors well known in the medical arts. For example, it is well within the skill of the art to start doses of the peptides at levels lower than those required to achieve the desired therapeutic effect and to gradually increase the dosage until the desired effect is achieved.

The form of the pharmaceutical compositions, the route of administration, the dosage and the regimen naturally depend upon the condition to be treated or prevented, the severity of the illness, the age, weight, and sex of the patient, etc.

The peptides and pharmaceutical compositions of the invention can be administered by any suitable route, in particular by parenteral, e.g., intravenous, intradermal, intracerebroventricular, subcutaneous, intramuscular, intraperitoneal, oral (e.g., buccal, inhalation, nasal and pulmonary spray), intradermal, transdermal (topical), transmucosal or intraocular route.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

The present invention will be further illustrated by the figures and examples below.

BRIEF DESCRIPTION OF THE SEQUENCES

| SEQ ID | Description | Sequence |
|---|---|---|
| 1 | Consensus sequence | HGEGSFX$_7$SDX$_{10}$SX$_{12}$X$_{13}$LDKLAARDFVNWLLQTK |
| 2 | Longer consensus sequence | HGEGSFX$_7$SDX$_{10}$SX$_{12}$X$_{13}$LDKLAARDFVNWLLQTKITD |
| 3 | Peptide GL-0001 | HGEGSFGSDMSIALDKLAARDFVNWLLQTKITD |
| 4 | Peptide GL-0007 | HGEGSFGSDFSIALDKLAARDFVNWLLQTK-NH$_2$ |
| 5 | Peptide GL-0001-Tag | HGEGSFGSDMSIALDKLAARDFVNWLLQTKITDGAADDDDDD |
| 6 | Peptide GL-0002 | HGEGSFVSDMSIVLDKLAARDFVNWLLQTK-NH$_2$ |
| 7 | Peptide GL-0003 | HGEGSFVSEMSIVLDKLAARDFVNWLLQTK-NH$_2$ |
| 8 | Peptide GL-0004 | HGEGSFVSDMSVVLDKLAARDFVNWLLQTK-NH$_2$ |
| 9 | Peptide GL-0005 | HGEGSFVSDLSVVLDKLAARDFVNWLLQTK-NH$_2$ |
| 10 | Peptide GL-0006 | HGEGSFVSDFSVVLDKLAARDFVNWLLQTK-NH$_2$ |
| 11 | Peptide GL-0008 | HGEGSFTSDFSIALDKLAARDFVNWLLQTK-NH$_2$ |

-continued

| SEQ ID | Description | Sequence |
|---|---|---|
| 12 | Peptide GL-0009 | HGEGSFVSDFSIALDKLAARDFVNWLLQTK-NH$_2$ |
| 13 | Peptide tag | GAADDDDDD |
| 14 | Peptide Co-3 of WO2018/069442 | HADGTFISDYSTILDNLAARDFINWLIQTKITD |
| 15 | Peptide Co-7 of WO2018/069442 | HAEGTFISDYSIAMDKLAARDFINWLIQTKITD |
| 16 | Peptide Co-19 of WO2018/069442 | HADGTFISDYSTILDNLAARDFINWLIQTKGKK |

BRIEF DESCRIPTION OF THE FIGURES

FIG. 1: In silico strategy for the design of double GIP/GLP-2 analogues. The final goal was to obtain a consensus sequence with at least 50% homology between the sequence and human GIP$_{1-30}$ or human GLP-2. Lower case letters at step 3 represent n: negatively charged amino acid, p: polar amino acid and a: aliphatic amino acid.

FIG. 2: Collagen maturity was evaluated in MC3T3-E1 cultures in the presence of vehicle (CTRL), or 200 nM [D-Ala$^2$]-GIP$_{1-30NH2}$ (GIP), [Gly$^2$]-GLP-2 (GLP-2) or both molecules (GIP+GLP-2). *: p<0.05 and ***: p<0.001 vs. vehicle-treated-cultures; $$: p<0.01 vs. [D-Ala$^2$]GIP$_{1-30NH2}$-treated cultures, and #: p<0.05 vs. [Gly$^2$]-GLP-2-treated-cultures.

FIG. 3: The number of newly-generated osteoclasts per well (N.Oc/well) was evaluated in human peripheral blood mononuclear cells isolated from healthy individuals and cultured in the presence of 25 ng/ml human M-CSF and 50 ng/ml human soluble RANKL (MR). This parameter was also evaluated in MR-treated cultures supplemented with 1 nM [D-Ala$^2$]-GIP$_{1-30NH2}$ (GIP), [Gly$^2$]-GLP-2 (GLP-2) or both molecules (GIP+GLP-2). ***: p<0.001 vs. MR; $: p<0.05 and $$$: p<0.001 vs. [D-Ala$^2$]GIP$_{1-30NH2}$-treated cultures, and ###: p<0.001 vs. [Gly$^2$]-GLP-2-treated-cultures.

FIG. 12: Trabecular bone strength was evaluated by compression test of vertebral bodies of the second lumbar vertebra.

FIG. 13: Trabecular bone microarchitecture was evaluated in vertebral bodies of the fifth lumbar vertebra. Animals were either treated with vehicle (OVX+Veh), 25 nmoles/kg/day GL-0001 (OVX+GL-0001), 25 nmoles/kg/day GL-0007 (OVX+GL-0007_25), 100 nmoles/kg/day GL-0007 (OVX+GL-0007_100) or once 100 µg/kg zoledronic acid (OVX+Zol). The studied features were as follows: BV/TV: Bone volume fraction, Tb.N: trabecular number, Tb.Th:trabecular thickness, Tb.Sp: trabecular separation. *: p<0.05 and **: p<0.01 vs. OVX+Veh.

FIG. 16: HEK-293 cells were transfected with a plasmid encoding the human GIPr. Production of cyclic AMP was recorded by FRET using the H74 probe. An increase in FRET ratio 470/530 nm indicates higher cAMP. [D-Ala$^2$] GIP$_{1-30NH2}$, [Gly$^2$]GLP-2, GL-0001 or a vehicle were added in the cultures and the levels of cAMP were recorded 30 min after. ***: p<0.001 vs. vehicle; ###: p<0.001 vs. [Gly$^2$] GLP-2.

FIG. 17: HEK-293 cells were transfected with a plasmid encoding the human GLP-2r. Production of cyclic AMP was recorded by FRET using the H74 probe. An increase in FRET ratio 470/530 nm indicates higher cAMP. [D-Ala$^2$] GIP$_{1-30NH2}$, [Gly$^2$]GLP-2, GL-0001 or a vehicle were added in the cultures and the levels of cAMP were recorded 30 min after. : p<0.01 and *: p<0.001 vs. vehicle; $: p<0.05 and $$: p<0.01 vs. [D-Ala$^2$]GIP$_{1-30NH2}$.

FIG. 18: HEK-293 cells were transfected with a plasmid encoding the human GIPr and the human GLP-2r. Production of cyclic AMP was recorded by FRET using the H74 probe. An increase in FRET ratio 470/530 nm indicates higher cAMP. [D-Ala$^2$]GIP$_{1-30NH2}$, [Gly$^2$]GLP-2, GL-0001 or a vehicle were added in the cultures and the levels of cAMP were recorded 30 min after. ***: p<0.001 vs. vehicle; ###: p<0.001 vs. [Gly$^2$]GLP-2; $$$: p<0.001 vs. [D-Ala$^2$] GIP$_{1-30NH2}$.

FIG. 19: Sequence alignment between the peptides of the invention and peptides disclosed in WO2018/069442.

FIG. 21: Evolution of combination index (CI) over dose range for collagen maturity.

EXAMPLES

Figure 2:
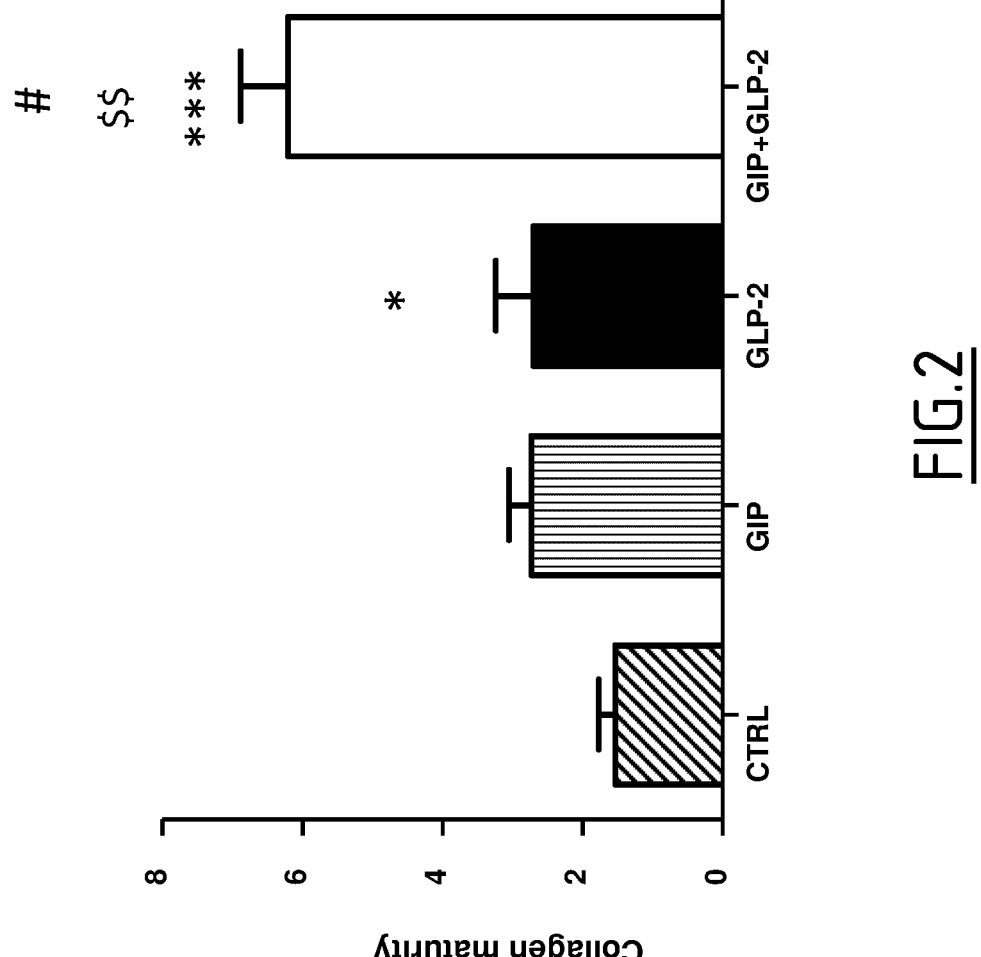
FIGS. 2-3: Effects of joint administration of GIP and GLP-2 on collagen maturity and number of osteoclasts.

Example 1: Design of the Peptides of the Invention

Materials and Methods

A full detail of all steps is provided in FIG. 1. Amino acid sequence of human GIP (accession #: P09681) and human GLP-2 (accession #: P01275.3) were collected from NCBI website (www.ncbi.nlm.nih.gov/protein). Amino acid sequence of known GLP-2 analogues namely Teduglutide (PubChem CID: 16139605), Elsiglutide, ZP1848 and FE 203799 were also collected (Wisniewski et al. (2016) *J. Med. Chem.* 59:3129-3139). Protein sequences were aligned manually using Word 2013 software. Analyses of homology percentage were conducted in Matlab R2016b with the Needleman-Wunsch algorithm. Threshold in sequence homology for validation was set at >50% homology with either GIP$_1$. 30 or GLP-2.

Results

FIG. 1 represents the in silico strategy used to design double GIP/GLP-2 analogues.

In step 1, a sequence alignment between human GIP$_{1-30}$ and human GLP-2 has been conducted manually in Word 2013 and led to the generation of the consensus sequence 1 (CS1) that corresponds to the same amino acid at the same sequence position. CS1 is composed of Ala$^2$, Gly$^4$, Phe$^6$, Asp$^{15}$, Asp$^{21}$, Phe$^{22}$, Asn$^{24}$, Trp$^{25}$, Leu$^{26}$ and Lys$^{30}$, respectively.

In step 2, the four known GLP-2 analogues, namely teduglutide, elsiglutide, ZP1848 and FE 203799 were also manually sequence aligned in order to establish the consensus sequence 2 (CS2). CS2 is composed of His$^1$, Gly$^2$, Gly$^4$, Phe$^6$, Ser$^7$, Glu$^9$, Thr$^{12}$, Ile$^{13}$, Leu$^{14}$, Asp$^{15}$, Leu$^{17}$, Ala$^{18}$, Ala$^{19}$, Arg$^{20}$, Asp$^{21}$, Phe$^{22}$, Ile$^{23}$, Trp$^{25}$, Leu$^{26}$, Ile$^{27}$, Thr$^{29}$, Lys$^{30}$, Ile$^{31}$, Thr$^{32}$ and Asp$^{33}$.

In step 3, human GIP$_{1-30}$ and human GLP-2 were sequence aligned manually to determine the class of amino acid in missing position of the CS1. When an amino acid from the same class has been encountered in both sequences at the same position, its class was indicated in sequence consensus 3 (CS3). It appeared that in both peptide sequences in position 3, 5, 9, 11, 13, 14, 17, 23, 27 and 29 were found negatively charged, polar, negatively charged, polar, aliphatic, aliphatic, aliphatic, aliphatic, aliphatic and polar amino acids, respectively.

In step 4, the inventors compared CS1 and CS2 in order to establish a sequence that could lead to a GLP-2 analogue. From this comparison was built the sequence consensus 4 (CS4) that contains His$^1$, Gly$^4$, Phe$^6$, Ser$^7$, Glu$^9$, Thr$^{12}$, Ile$^{13}$, Leu$^{14}$, Asp$^{15}$, Leu$^{17}$, Ala$^{18}$, Ala$^{19}$, Arg$^{20}$, Asp$^{21}$, Phe$^{22}$, Ile$^{23}$, Asn$^{24}$, Trp$^{25}$, Leu$^{26}$, Ile$^{27}$, Thr$^{29}$, Lys$^{30}$, Ile$^{31}$, Thr$^{32}$, Asp$^{33}$.

In step 5, the inventors aligned CS4 with CS3 in order to verify whether amino acids at position 3, 5, 9, 11, 13, 14, 17, 23, 27 and 29 were of the correct class. CS4 was then validated.

The inventors next performed in step 6 analyses of sequence homology from one side between human GIP$_{1-30}$ and CS4 and on the other side between human GLP-2 and CS4. The inventors evidenced that CS4 had a great sequence homology with human GLP-2 (76%) but a poor homology with human GIP$_{1-30}$ (27%).

They next adjusted CS4 at positions 2, 3, 5, 8, 10, 11, 16 and 28 resulting in consensus sequence 7 (CS7) as follows, His$^1$, Gly$^2$, Glu$^3$, Gly$^4$, Thr$^5$, Phe$^6$, Ser$^7$, Ser$^8$, Glu$^9$, Ser$^{11}$, Thr$^{12}$, Ile$^{13}$, Leu$^{14}$, Asp$^{15}$, Lys$^{16}$, Leu$^{17}$, Ala$^{18}$, Ala$^{19}$, Arg$^{20}$, Asp$^{21}$, Phe$^{22}$, Ile$^{23}$, Asn$^{24}$, Trp$^{25}$, Leu$^{26}$, Ile$^{27}$, Ala$^{28}$, Thr$^{29}$, Lys$^{30}$, Ile$^{31}$, Thr$^{32}$ and Asp$^{33}$. It is worth noting that Gly$^2$ was chosen to confer dipeptidyl-peptidase-4 resistance.

Again, the inventors checked the sequence homology with human GIP$_{1-30}$ and human GLP-2 and found 45% and 76%, respectively. However, as their goal was to obtain at least 50% homology with both human molecules, they remodified CS7 to incorporate more homology with human GIP$_{1-30}$. Modifications were made at positions 5, 7, 9, 12, 13, 23, 27, 28 and 31-33. This led to consensus sequence 9 (CS9) that is His$^1$, Gly$^2$, Glu$^3$, Gly$^4$, Sers, Phe$^6$, Ser$^8$, Asp$^9$, Ser$^{11}$, Leu$^{14}$, Asp$^{15}$, Lys$^{16}$, Leu$^{17}$, Ala$^{18}$, Ala$^{19}$, Arg$^{20}$, Asp$^{21}$, Phe$^{22}$, Val$^{23}$, Asn$^{24}$, Trp$^{25}$, Leu$^{26}$, Leu$^{27}$, Asn$^{28}$, Thr$^{29}$ and Lys$^{30}$ with a terminal amidation. From the literature, it seemed that Ile$^{31}$, Thr$^{32}$ and Asp$^{33}$ were not necessary if Lys$^{30}$ was amidated (Wisniewski et al. (2016) *J. Med. Chem.* 59:3129-3139). They also decided that at positions 7, 10, 12 and 13 it could be any amino acid in order to play on the receptor binding capacity and biological activity.

They next compared CS9 with human $GIP_{1-30}$ and human GLP-2 and found more than 50% homology for both molecules, which led to the validation of CS9.

Example 2: Effect of the Peptides of the Invention on Bone Remodeling

Materials and Methods

1. Reagents

All analogues were purchased from GeneCust Europe with a purity >95% (Dudelange, Luxembourg). Purity has been verified by high performance liquid chromatography and peptide composition validated by mass spectroscopy. Murine MC3T3-E1 subclone 4, murine Raw 264.7 and human HEK-293 cells were purchased from American type culture collection (ATCC, Teddington, UK). Buffy coat from healthy individuals were obtained from Etablissement frangais du sang (Angers, France). Human and murine receptor activator of nuclear factor kB ligand (RANKL) and human macrophage colony stimulating factor (M-CSF) were purchased from R&D Systems Europe (Abingdon, UK). Human GIP receptor and human GLP-2 receptor cDNAs were purchased from Addgene (plasmid 14942, kindly donated by B. Thorens) and the PlasmID Repository (plasmid HsCD00346244), respectively. All other chemicals were obtained from Sigma-Aldrich (Lyon, France) unless otherwise stated.

2. Cell Culture

Murine MC3T3-E1 subclone 4 cells were grown and expanded in propagation medium containing alpha minimum essential medium (αMEM) supplemented with 5% fetal bovine serum (FBS), 5% bovine calf serum, 100 U/mL penicillin, and 100 µg/mL streptomycin in a humidified atmosphere enriched with 5% $CO_2$ at 37° C.

Murine Raw 264.7 and human HEK-293 cells were grown and expanded in propagation medium containing Dulbecco's modified Eagle medium (DMEM) supplemented with 10% fetal bovine serum (FBS), 100 U/mL penicillin, and 100 µg/mL streptomycin in a humidified atmosphere enriched with 5% $CO_2$ at 37° C.

3. Cell Death Assay

Increased plasma membrane permeability that occurs during cell death can be visualised using trypan blue, a dye that is excluded from living cells and is incorporated into the cells when they are undergoing death (Bellido and Plotkin (2008) *Methods Mol. Biol.* 455:51-75).

Briefly, MC3T3-E1 cells were plated in 24 well-plates and cultured in the presence of saline, various concentrations of GL-0001 or $10^{-6}$M rosiglitazone, a drug known to increase bone cell death (Mieczkowska et al. (2012) *J. Biol. Chem* 287:23517-23526). After 24 h, the cell culture supernatant containing the floating cells was collected and put in previously labelled eppendorf tubes. Each well was washed in PBS before trypsin was added to detach adherent cells. The mixture containing detached adherent cells was collected and pooled in the eppendorf containing the cell culture supernatant. Cells were spun at 1,500 rotation per minute (rpm) for 10 minutes, the supernatant was removed carefully and cells were incubated with trypan blue 0.04% and transferred into a haemocytometer. Living (clear) and dead (blue) cells were counted under light microscope examination and the percentage of dead cells was determined for each condition as follow: % of dead cells=100×(Number of dead cells)/(Number of dead cells+Number of living cells)

4. Osteoclast Assay

Human peripheral blood mononuclear cells were isolated from 3 buffy coats obtained at the Etablissement Francais du Sang (Angers, France) as described in Mabilleau and Sabokbar (2009) PLoS One 4:e4173.

Blood was diluted 1:1 in α-minimal essential medium (MEM) (Invitrogen, Paisley, UK), layered over Histopaque and centrifuged (700×g) for 20 min. The interface layer was resuspended in MEM then centrifuged (600×g) for a further 10 min after which the resultant cells were resuspended in media supplemented with 10% heat inactivated foetal calf serum (FCS, Invitrogen, Paisley, UK) and counted in a haemocytometer following lysis of red blood cells using a 5% (v/v) acetic acid solution.

To assess the extent of osteoclast formation, isolated human PBMCs were cultured in 24-well plates in MEM containing 100 UI/ml penicillin, 100 µg/ml streptomycin and 10% FCS (osteoclast medium) (Mabilleau et al. (2011) *J Biol Chem* 286:3242-3249). After 2 h incubation, cultures were vigorously rinsed in medium to remove non-adherent cells, and then maintained in 1 ml MEM/FCS with 25 ng/ml recombinant human M-CSF, 50 ng/ml recombinant human sRANKL (added at day 7) and various concentrations of gut hormone analogues (added at day 7). Cultures were terminated after 14 days to assess the extent of osteoclast formation (TRAcP staining as described below). All factors were replenished every 2-3 days.

Murine Raw 264.7 cells were scrapped off the plastic dish, plated at a density of $1.25×10^4$ cells/cm$^2$ and grown in propagation medium enriched with 10 ng/ml soluble murine RANKL. After 110 h, cells were fixed with formalin (10% in PBS buffer) for 10 minutes and rinsed in distilled water prior to TRAcP staining.

5. TRAcP Staining

Tartrate resistant acid phosphatase (TRAcP) was histochemically revealed by a simultaneous coupling reaction using Naphtol AS-BI-phosphate as substrate and Fast violet B as the diazonium salt for 90 minutes at 37° C. in the dark. Cultures were rinsed three times in distilled water and the residual activity was inhibited by 4% NaF for 30 minutes. Cells were then rinsed in distilled water, counterstained with DAPI for 20 minutes and allowed to dry before mounting using an aqueous medium. TRAcP positive cells, with more than three nuclei, were identified as osteoclasts. The number of newly generated were assessed using light microscopic examination.

6. Collagen Maturity Assay

For collagen maturity assay, cells were detached with trypsin-EDTA, plated at a density of $1.5×10^4$ cells/cm$^2$ and grown to confluence in propagation medium. At confluence, the propagation medium was replaced by the differentiation medium containing αMEM supplemented with 5% FBS, 5% bovine calf serum, 100 U/mL penicillin, 100 µg/mL streptomycin, 50 µg/ml ascorbic acid and various concentrations of analogues. This day was considered as day 1. The differentiation medium was replenished every two days.

At day 14, osteoblast cultures were decellularized by incubation in 0.2 M sodium cacodylate buffer (pH 7.4) containing 0.1% triton X100 for 4 h on an orbital shaker. Cultures were rinsed at least six times with milliQ water, fixed in absolute ethanol, scrapped off the culture dish and transferred onto BaF2 windows where they were air-dried.

Integrity of the collagen extracellular matrix was verified by comparing the obtained Fourier transform infrared spectrum with those of commercial collagen.

Spectral analysis was performed using a Bruker Vertex 70 spectrometer (Bruker optics, Ettlingen, Germany) interfaced with a Bruker Hyperion 3000 infrared microscope equipped with a standard single element Mercury Cadmium Telluride (MCT) detector.

Infrared spectra were recorded at a resolution of 4 cm$^{-1}$, with an average of 32 scans in transmission mode. Background spectral images were collected under identical conditions from the same BaF2 windows at the beginning and end of each experiment to ensure instrument stability. At least 20 spectra were acquired for each condition and analyzed with a lab-made routine script in Matlab R2016b (The Mathworks, Natick, MA). The collagen maturity index was determined as the relative ratio of mature pyridinium to immature dehydrodihydroxylysinonorleucine collagen cross-links using their respective subbands located at 1660 cm$^{-1}$ and 1690 cm$^{-1}$ of the amide I peak.

7. Binding Assay

Human HEK-293 cells were plated at a density of $2 \times 10^5$ cells/cm$^2$ in 10 cm petri dishes. After 24 h, cells were transfected with an optimized calcium phosphate method using 15 µg plasmid DNA encoding either the human GIP receptor or the human GLP-2 receptor. Twenty-four hours after transfection, transfected cells were detached and plated at a density of $6 \times 10^4$ cells/cm$^2$ in black 96 well plates with clear bottom (Ibidi GmbH, Martinsried, Germany). After 24 h, various concentrations of analogues were added in each well in the presence of either $10^{-7}$M Fam-[D-Ala$^2$]-GIP$_{1-30}$ or $10^{-6}$M Fam-[Gly$^2$]-GLP-2 in αMEM supplemented with 0.1% bovine serum albumin (BSA). Equilibrium binding was achieved overnight at 37° C. Cells were then washed twice with assay buffer and solubilized in 0.1 M NaOH.

Fluorescence was read with an M2 microplate reader (Molecular devices, Wokingham, UK) with excitation wavelength set up at 490 nm and emission wavelength set up at 525 nm.

Binding at the human GIP receptor or human GLP-2 receptor was achieved by non-linear regression analyses in GraphPad Prism 6.0.

8. Cyclic AMP Assay

Human HEK-293 cells were plated at a density of $2 \times 10^5$ cells/cm$^2$ in 4 well microslides (ibidi GmbH, Martinsried, Germany). After 24 h, cells were transfected with an optimized calcium phosphate method using 10 µg plasmid DNA encoding either the human GIP receptor or the human GLP-2 receptor and 5 µg of plasmid DNA encoding the mTurquoise-EPAC-$^{cP173}$Venus-Venus H74 probe, kindly provided by Professor K. Jalink (Netherland Cancer Institute, Amsterdam, Netherland). In co-transfection experiments, cells were transfected with 5 µg plasmid DNA encoding the human GIP receptor, 5 µg plasmid DNA encoding the human GLP-2 receptor and 5 µg of plasmid DNA encoding the H74 probe. Twenty-four hours after transfection, transfected cells were rinsed in phosphate buffer saline and incubated in HEPES buffered saline (containing 140 mM NaCl, 5 mM KCl, 1 mM MgCl$_2$, 1 mM CaCl$_2$, 10 mM glucose, 10 mM HEPES) in a chamber containing a Leica imaging system (DMI6000 Inverted microscope fitted with a SP8 confocal head) and a controlled atmosphere (37° C., 5% CO$_2$). The image acquisition was performed with a 63 X, 1.4 N.A. oil immersion objective and a Hybrid® detector (Leica) and images were collected after 30 minutes. Donor excitation was made with a 458 nm Ar laser, donor emission was collected between 460-505 nm and acceptor emission between 520-600 nm by setting the SP8 spectrometer accordingly. FRET was expressed as the ratio between donor and acceptor signals. The FRET value was set at 1 at the onset of the experiment. Vehicle, $10^{-9}$ M [D-Ala$^2$]-GIP$_{1-}$ $_{30}$, $10^{-9}$M [Gly$^2$]-GLP-2 or $10^{-9}$ M GL-0001 were added in the assay medium and the FRET signal was measured as above.

9. Animals

BALB/c (BALB/cJRj) mice were obtained from Janvier Labs (Saint-Berthevin, France). All animal experiments were approved by the French ministry of higher education, research and innovation under the license 6154-201607211130415v1.

Mice were housed 4 animals per cage in the institutional animal lab (Agreement E49007002) at 24° C.+/−2° C. with a 12-hour light/dark cycle, and were provided with tap water and normal diet (Diet A04, Safe, Augy, France) ad libitum until sacrifice by cervical dislocation. All procedures were conducted according to the French Animal Scientific Procedures Act 2013-118.

Bilateral ovariectomy (OVX) was performed in 40 BALB/c mice at 12 weeks of age under general anesthesia supplemented with a β2 adrenergic receptor agonist. At 16 weeks of age, ALZET osmotic pumps (model number 2006, Durect Corp., Cupertino, CA) filled with the below saline or peptide were implanted subcutaneously between the two scapula under general anesthesia in 32 mice. Successful filling of pumps was verified by weighting the pump before and after filling. At 20 weeks of age, ALZET osmotic pumps were replaced by similar pumps to ensure delivery for four new weeks. Mice were randomly allocated into four groups:

(i) vehicle daily (OVX+Veh, n=8),
    (ii) 25 nmoles/kg/day GL-0001 (OVX+GL-0001, n=8),
    (iii) 25 nmoles/kg/day GL-0007 (OVX+GL-0007_25, n=8),
    (iv) 100 nmoles/kg/day GL-0007 (OVX+GL-0007_100, n=8).

These doses of analogues were based on the inventors' extensive knowledge on gut hormone analogues (Mabilleau et al. (2014) *Bone* 63:61-68; Mansur et al. (2015) *J Cell Physiol* 230:3009-3018; Mieczkowska et al. (2015) *Bone* 74:29-36; Mabilleau et al. (2016) Bone 91:102-112; Mansur et al. (2016) *Bone* 87:102-113; Pereira et al. (2017) *Front Endocrinol* (*Lausanne*) 8:327; Mabilleau et al. (2018) J Endocrinol.). Unfortunately, a mouse from the 25 nmoles/kg/day died during osmotic pump replacement.

Eight additional OVX mice were used as positive controls (OVX+Zol) and were administered a single 100 µg/kg zoledronic acid (Reference number 6111, batch number 1A/203523, Tocris Bioscience, Bristol, UK) by intravenous injection in the tail vein. This dose and regimen of zoledronic acid was equivalent to the 5 mg infusion approved for the treatment of post-menopausal osteoporosis in humans.

Body weight was monitored once a week with a precision scale (Adventurer™ Pro, Ohaus, Nanikon, Switzerland). All mice were also administered with calcein (10 mg/kg; ip) 12 and 2 days before being culled at 24 weeks of age. After necropsy, femurs, second and fifth lumbar vertebra, liver and pancreas were collected and processed as detailed below.

10. Biomechanical Testings

At necropsy, femurs and second lumbar vertebras (L2) were cleaned of soft tissue and immediately frozen in a saline-soaked gauze at −20° C. Three-point-bending experiments were performed on femurs after thawing bones at 4° C. overnight.

Femur length was measured with a digital caliper (Mitutoyo, Roissy en France, France). No significant differences in femur length was observed between the groups.

Femurs were loaded to failure in 3-point bending at 2 mm/min using a servohydraulic materials testing system (Instron 5942, Instron, Elancourt, France). The lower span length was of 10 mm. Femurs were oriented so the anterior quadrant was facing down and subjected to tensile loads. Load and displacement of the upper crosshead, which were digitally recorded at a sampling rate of 100 Hz, were measured using a 500 N load cell (Instron). Stiffness, ultimate load, yield load, post-yield displacement (PYD), and work-to-fracture were calculated from the load-displacement curves. PYD was defined as the displacement at failure minus the displacement at yield. Yield was defined as the point where the regression representing a 0.2% reduction in stiffness intersected the load-displacement curve.

Compression experiments were performed on L2. Briefly, vertebral bodies were carefully dissected and glued with cyanoacrylate glue on a Plexiglas plate and then incubated in saline at 4° C. until use the next day. L2 vertebral bodies were compressed to failure at a displacement rate of 1 mm/min using an Instron 5942 device. Load and displacement of the upper plateau were recorded at a sampling rate of 100 Hz. Maximum load and stiffness were computerized from load-displacement curves.

11. Microcomputed/Nanocomputed X-Ray Tomography (MicroCT)

MicroCT analyses at the femur midshaft were performed with a Skyscan 1076 microtomograph (Bruker MicroCT, Kontich, Belgium) operated at 50 kV, 200 µA, 2000 ms integration time. The isotropic pixel size was fixed at 9 µm, the rotation step at 0.5° and exposure was done with a 0.5-mm aluminum filter. Each 3D reconstruction image dataset was binarized using global thresholding. Cortical volume of interest (VOI) was located 4 mm above the distal growth plate and extended 1 mm further up.

Analyses of vertebral bodies of the fifth lumbar vertebra (L5) were performed with a Nanotom nanotomograph (Phoenix, GE, USA) operated at 85 kV, 220 µA, 1000 ms integration time. The isotropic pixel size was fixed at 4 µm, the rotation step at 0.25° and exposure was done with a 0.1 mm copper filter. Each 3D reconstruction image dataset was binarized using global thresholding. Trabecular volume of interest was computerized on coronal sections of the L5 vertebral body. Trabecular VOI was spread over the entire vertebral body excluding the first and last 80 µm from the anterior and posterior cortical wall. All microCT/NanoCT parameters were determined according to guidelines and nomenclature proposed by the American Society for Bone and Mineral Research (Bouxsein et al., 2010).

12. Bone Composition Assessment

After three-point bending experiments, femurs were embedded undecalcified in pMMA at 4° C. One-micrometer cross-sectional sections of the midshaft femur were sandwiched between BaF2 optical windows and Fourier transform infrared imaging (FTIRI) assessment was performed in the posterior quadrant. FTIRI was performed with a vertex 70 spectrometer (Bruker, Ettlingen, Germany) interfaced with a Hyperion 3000 microscope and a focal plane array detector (64×64 pixels) covering a field of view of 180×180

µm. Nine field-of-view were stitched together to allow sufficient bone to be analyzed. Sections were scanned with a spectral resolution of 8 cm$^{-1}$ (spectral region 900-2000 cm$^{-1}$). Each spectrum was corrected for Mie scattering with the RMieS-EMSC_v5 algorithm (kind gift of Prof Peter Gardner, University of Manchester, UK) prior to be subjected to pMMA subtraction.

Evaluation of spectral images was done with a lab-made routine script in Matlab R2016b (The Mathworks, Natick, MA) as described in Aguado et al. (2017) *Calcif Tissue Int* 100:332-340.

FTIR bone parameters (Paschalis (2012) *Methods Mol Biol* 816:517-525) calculated were: (1) phosphate/amide ratio (area of v1, v3 phosphate/area amide1); (2) acid phosphate content (intensity ratio 1127 cm$^{-1}$/1096 cm$^{-1}$) (Spevak et al. (2013) *Calcif Tissue Int* 92:418-428); (3) mineral crystallinity (intensity ratio 1030 cm$^{-1}$/1020 cm$^{-1}$), reflecting crystal size and perfection; (4) crystal size index (intensity ratio 1075 cm$^{-1}$/1055 cm$^{-1}$), representing the crystal size in 002, 211, 200 and 202 directions (Gadaleta et al. (1996) *Calcif Tissue Int* 58:9-16) and (5) collagen maturity (intensity ratio 1660 cm$^{-1}$/1690 cm$^{-1}$).

The carbonate/phosphate ratio (intensity v3 carbonate located at ~1415 cm$^{-1}$/1030 cm$^{-1}$) was computed after subtracting the organic matrix spectrum (Ou-Yang et al. (2001) *J Bone Miner Res* 16:893-900). For each of the compositional parameters, the mean and full width at half maximum of the pixel distribution (excluding the zero background values) were computed and represented as mean and heterogeneity.

13. Histology

Liver and pancreas were collected at necropsy and immediately fixed in formalin. After paraffin embedding, 4-µm thick section were cut and stained with hematoxylin/phloxin staining. Histological observations have been made by a trained histologist in order to assess the presence of tissue abnormalities.

14. Statistical Analysis

Figure 3:
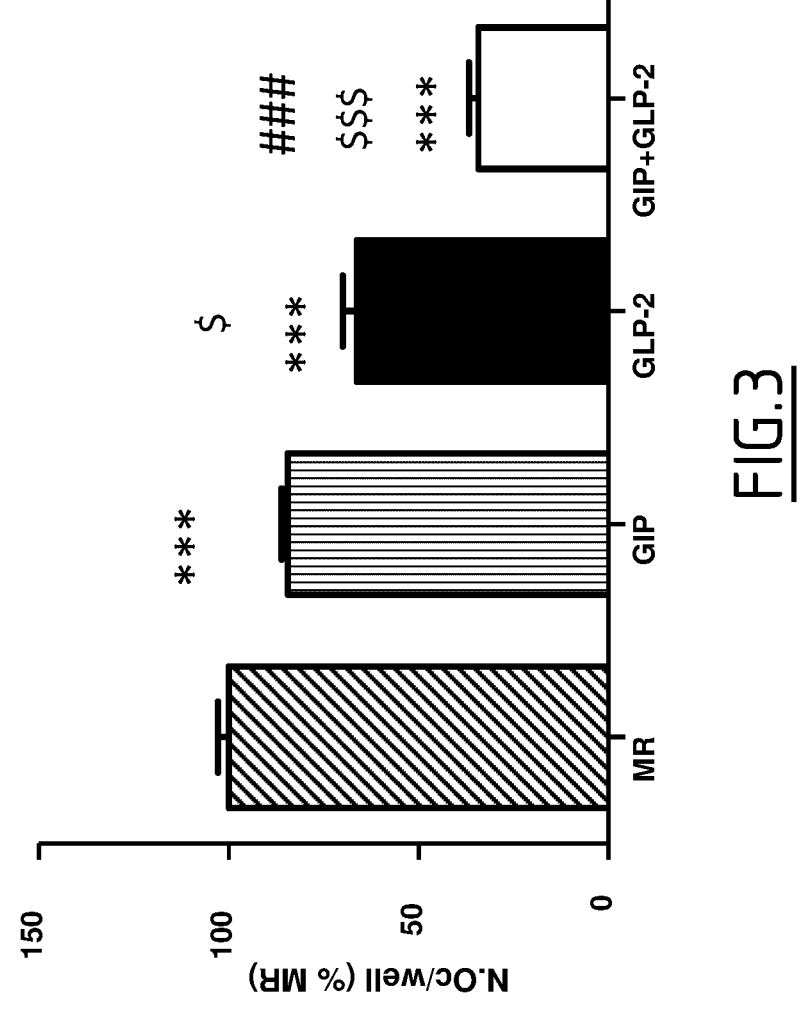
Figure 16:
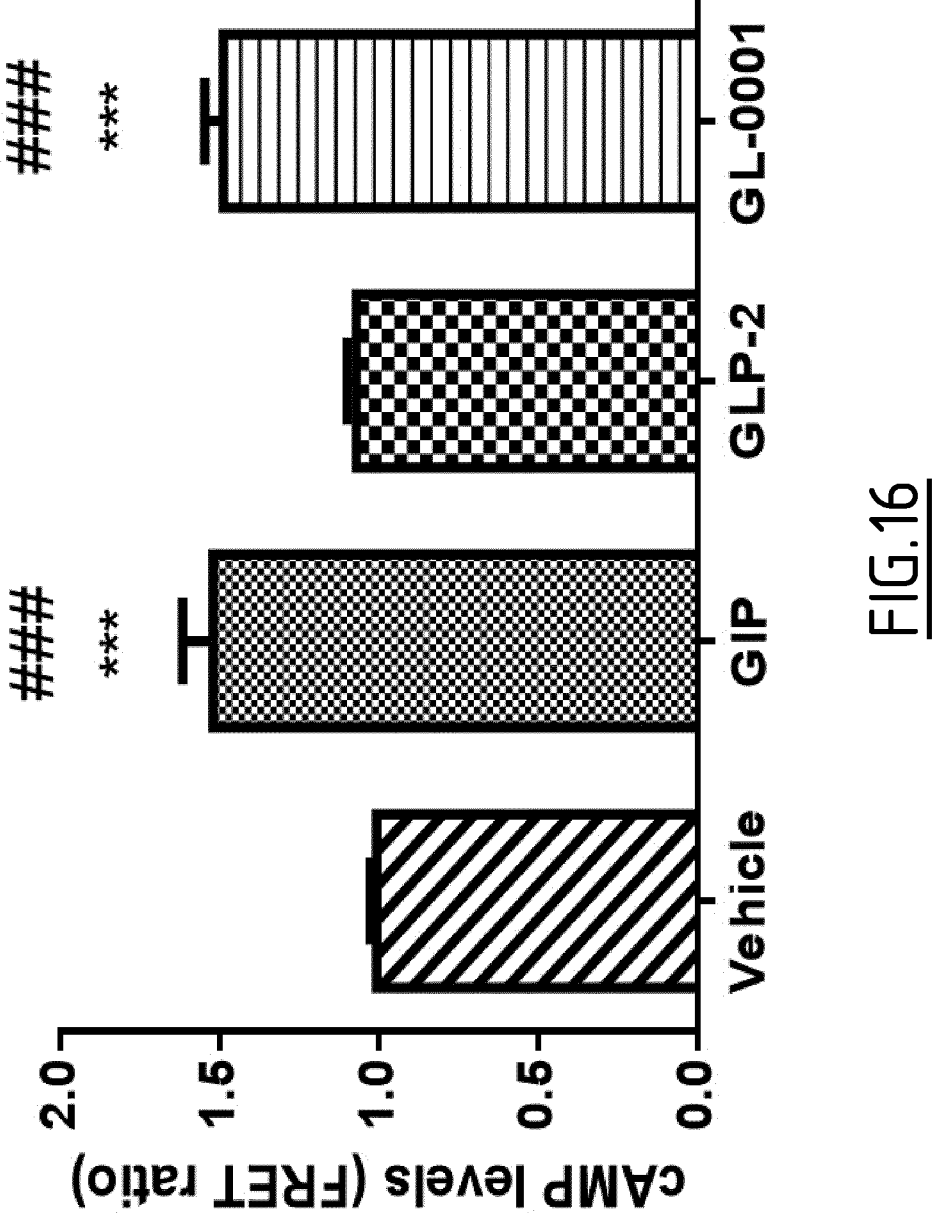
FIG. 16-18: Activation of the GIPr and GLP-2r.
Figure 17:
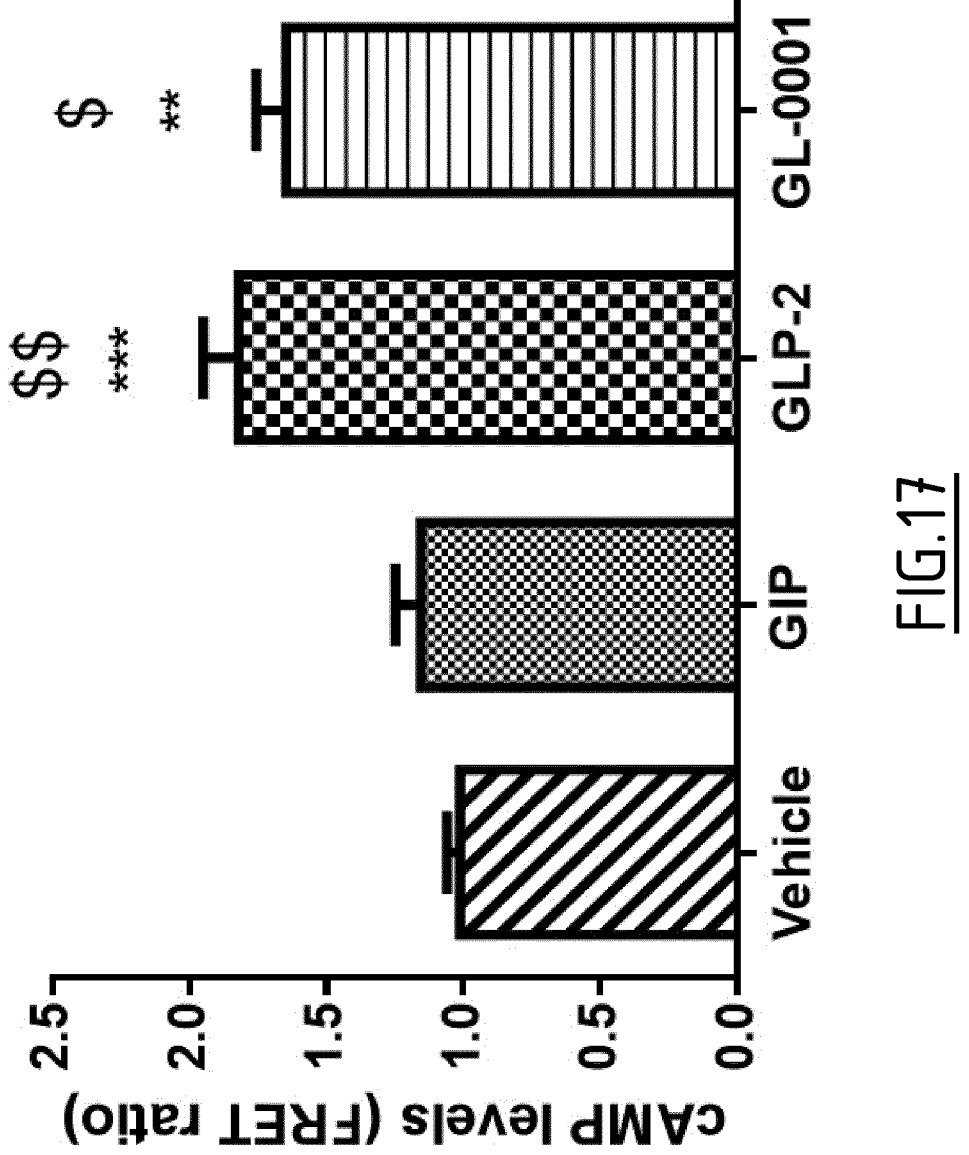
Figure 18:
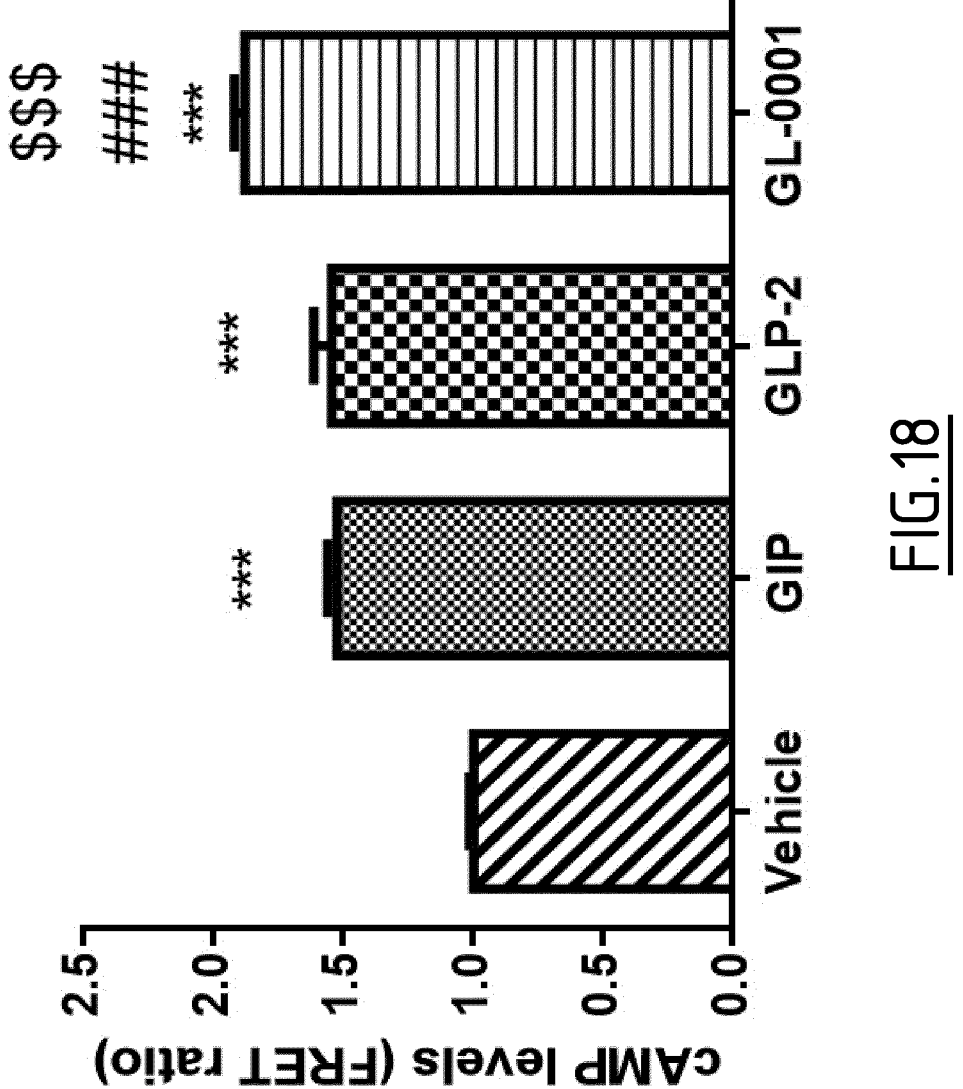

One-way analyses of variance with Holm-Sidak's multiple comparisons test, with a single pooled variance were used to compare differences in collagen maturity and number of osteoclast in FIGS. 2-3 as well as cAMP levels in FIGS. 16-18.

One-way analyses of variance with Dunnett multiple comparison test were employed to test for significance between OVX+Veh, OVX+GL-0001, OVX+GL-0007_25 and OVX+GL-0007_100 groups.

Differences at p equal to or less than 0.05 were considered significant.

Results

Based on the consensus sequence obtained as disclosed in Example 1, the following peptides were tested by the inventors.

TABLE 1

| Double analogues peptides | | | |
|---|---|---|---|
| Peptide | Sequence | Homology GIP | Homology GLP-2 |
| GL-0001 | HGEGSFGSDMSIALDKLAARDFVNWLLQTKITD (SEQ ID NO: 3) | 55% | 67% |
| GL-0001-Tag | HGEGSFGSDMSIALDKLAARDFVNWLLQTKITDGA ADDDDDD (SEQ ID NO: 5) | 43% | 52% |

TABLE 1-continued

| Double analogues peptides | | | |
|---|---|---|---|
| Peptide | Sequence | Homology GIP | Homology GLP-2 |
| GL-0002 | HGEGSFVSDMSIVLDKLAARDFVNWLLQTK$_{-NH2}$ (SEQ ID NO: 6) | 57% | 58% |
| GL-0003 | HGEGSFVSEMSIVLDKLAARDFVNWLLQTK$_{-NH2}$ (SEQ ID NO: 7) | 53% | 61% |
| GL-0004 | HGEGSFVSDMSVVLDKLAARDFVNWLLQTK$_{-NH2}$ (SEQ ID NO: 8) | 53% | 58% |
| GL-0005 | HGEGSFVSDLSVVLDKLAARDFVNWLLQTK$_{-NH2}$ (SEQ ID NO: 9) | 53% | 55% |
| GL-0006 | HGEGSFVSDFSVVLDKLAARDFVNWLLQTK$_{-NH2}$ (SEQ ID NO: 10) | 53% | 55% |
| GL-0007 | HGEGSFGSDFSIALDKLAARDFVNWLLQTK$_{-NH2}$ (SEQ ID NO: 4) | 60% | 55% |
| GL-0008 | HGEGSFTSDFSIALDKLAARDFVNWLLQTK$_{-NH2}$ (SEQ ID NO: 11) | 60% | 55% |
| GL-0009 | HGEGSFVSDFSIALDKLAARDFVNWLLQTK$_{-NH2}$ (SEQ ID NO: 12) | 60% | 55% |

1. Effects of Joint Administration of GIP and GLP-2 on Collagen Maturity and Number of Osteoclasts FIG. 2 presents the effects of vehicle (CTRL), [D-Ala$^2$]-GIP$_{1-30NH2}$, [Gly$^2$]-GLP-2 or joint administration of [D-Ala$^2$]-GIP$_{1-30NH2}$ and [Gly$^2$]-GLP-2 on collagen maturity.

[D-Ala$^2$]-GIP$_{1-30NH2}$ or [Gly$^2$]-GLP-2 were capable of increasing collagen maturity to approximately 82% (p=0.074) or 111% (p=0.0246), respectively. The joint administration of [D-Ala$^2$]-GIP$_{1-30NH2}$ and [Gly$^2$]-GLP-2 resulted in a significant increase (255%, p<0.001) in this parameter. This increase was also significantly greater than observed with [D-Ala$^2$]GIP$_{1-30NH2}$ or [Gly$^2$]-GLP-2 alone.

FIG. 3 presents the effects of vehicle (CTRL), [D-Ala$^2$]-GIP$_{1-30NH2}$, [Gly$^2$]-GLP-2 or joint administration of [D-Ala$^2$]-GIP$_{1-30NH2}$ and [Gly$^2$]-GLP-2 on human osteoclast formation in vitro. Here again, [D-Ala$^2$]-GIP$_{1-30NH2}$ and [Gly$^2$]-GLP-2 were potent to significantly reduced osteoclast formation by 16% (p<0.001) and 34% (p<0.001), respectively. Joint administration of these molecules led to a significant 66% reduction (p<0.001) in osteoclast formation.

2. Effects of GL-0001 on Osteoblast Cell Death.

Figure 4:
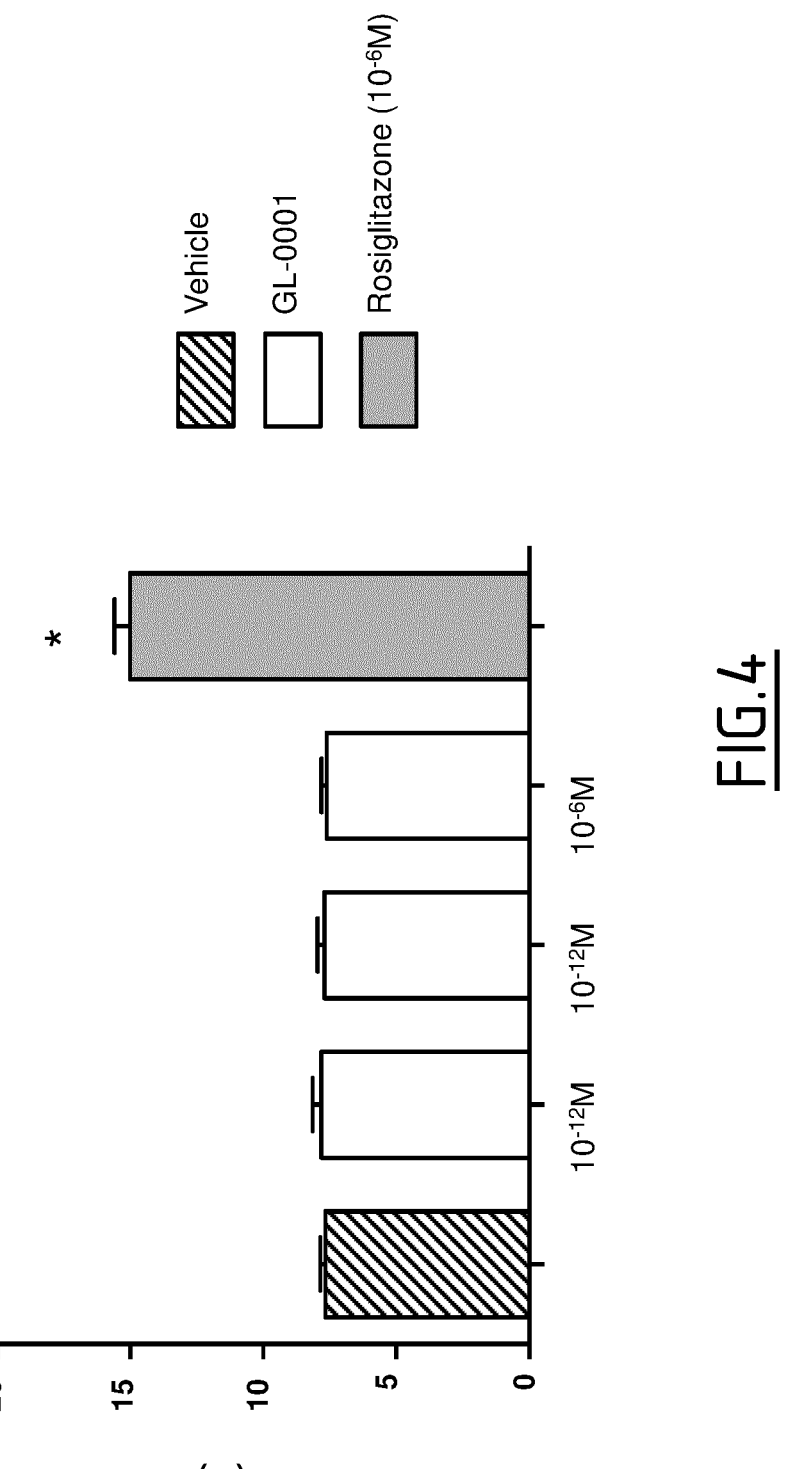
FIG. 4: Effects of GL-0001 on osteoblast cell death. Murine MC3T3-E1 cells were cultured for 24 hrs in the presence of saline, various concentrations of GL-0001 or 10$^{-6}$ M rosiglitazone. *: p<0.05 vs. saline-treated cultures.

FIG. 4 presents the results on MC3T3-E1 cell death in the presence of vehicle, GL-0001 or rosiglitazone. The inventors previously shown that rosiglitazone administration results in increase cell death and as such was used in this assay as a positive inductor of cell death.

This figure shows that GL-0001 at concentration as high as $10^{-6}$ M does not induce cell death, in opposition to rosiglitazone.

3. Binding Affinity of Double Analogues at the Human GIP Receptor and their Respective IC50.

The inventors determined the binding affinities of [D-Ala$^2$]GIP$_{1-30NH2}$ or the double analogues peptides disclosed in Table 1 above at the human GIP receptors. The corresponding IC50 determined for each compound was as follows:

TABLE 2

| IC50 towards GIP receptor | |
|---|---|
| | IC50 (nM) |
| [D-Ala$^2$]GIP$_{1-30NH2}$ | 0.97 ± 0.29 |
| GL-0001 | 1.19 ± 0.53 |
| GL-0002 | 2.78 ± 0.82 |
| GL-0003 | 0.72 ± 0.15 |
| GL-0004 | 37.85 ± 14.8 |
| GL-0005 | 0.14 ± 0.04 |
| GL-0006 | 4.60 ± 1.25 |
| GL-0007 | 1.05 ± 0.41 |
| GL-0008 | 0.91 ± 0.25 |
| GL-0009 | 13.05 ± 3.14 |

From IC50 values, the potency of the different analogues tested appeared as GL-0005>GL-0003>GL-0008>[D-Ala$^2$]GIP$_{1-30NH2}$>GL-0007>GL-0001>GL-0002>GL-0006>GL-0009>GL-0004.

4. Binding Affinity of Double Analogues at the Human GLP-2 Receptor and their Respective IC50.

The inventors determined the binding affinities of [Gly$^2$]GLP-2 or the double analogues peptides disclosed in Table 1 above at the human GLP-2 receptors. The corresponding IC50 determined for each compound was as follows:

TABLE 3

| IC50 towards GLP-2 receptor | |
|---|---|
| | IC50 (nM) |
| [Gly$^2$]GLP-2 | 0.19 ± 0.04 |
| GL-0001 | 0.44 ± 0.12 |
| GL-0002 | 15.16 ± 3.00 |
| GL-0003 | 22.86 ± 3.67 |
| GL-0004 | 0.07 ± 0.02 |
| GL-0005 | 15.05 ± 4.93 |
| GL-0006 | 1.04 ± 0.20 |
| GL-0007 | 0.57 ± 0.17 |

TABLE 3-continued

| IC50 towards GLP-2 receptor | |
| --- | --- |
| | IC50 (nM) |
| GL-0008 | 14.74 ± 5.69 |
| GL-0009 | 53.01 ± 11.9 |

From IC50 values, the potency of the different analogues tested appeared as GL-0004>[Gly$^2$]GLP-2>GL-0001>GL-0007>GL-0006>GL-0008>GL-0005>GL-0002>GL-0003>GL-0009.

5. Effects of Double Analogue on Osteoclast Formation In Vitro and their Respective IC50.

The inventors determined the effects of [D-Ala$^2$]-GIP$_{1-30NH2}$, [Gly$^2$]-GLP-2 or the double analogues peptides disclosed in Table 1 on Raw264.7 cell-mediated osteoclast formation in vitro.

The corresponding IC50 determined for each compound was as follows:

TABLE 4

| IC50 on osteoclast formation | |
| --- | --- |
| | IC50 (pM) |
| [D-Ala$^2$]-GIP$_{1-30NH2}$ | 40.1 ± 10.6 |
| [Gly$^2$]GLP-2 | 32.2 ± 15.1 |
| GL-0001 | 18.2 ± 5.6 |
| GL-0001-Tag | 2144 ± 25670 |
| GL-0002 | 1520 ± 3288 |
| GL-0003 | 4631 ± 12784 |
| GL-0004 | 11.6 ± 6.1 |
| GL-0005 | 10.7 ± 9.7 |
| GL-0006 | 9.6 ± 4.3 |
| GL-0007 | 36.0 ± 11.2 |
| GL-0008 | 16.8 ± 4.2 |
| GL-0009 | 180.5 ± 307.1 |

From IC50 values, the potency of the different analogues tested appeared as GL-0006>GL-0005>GL-0004>GL-0008>GL-0001>[Gly$^2$]GLP-2>GL-0007>[D-Ala$^2$]GIP$_{1-30NH2}$>GL-0009>GL-0002>GL-0001-Tag>GL-0003.

6. Effects of Double Analogue on Collagen Maturity In Vitro.

Figure 5:
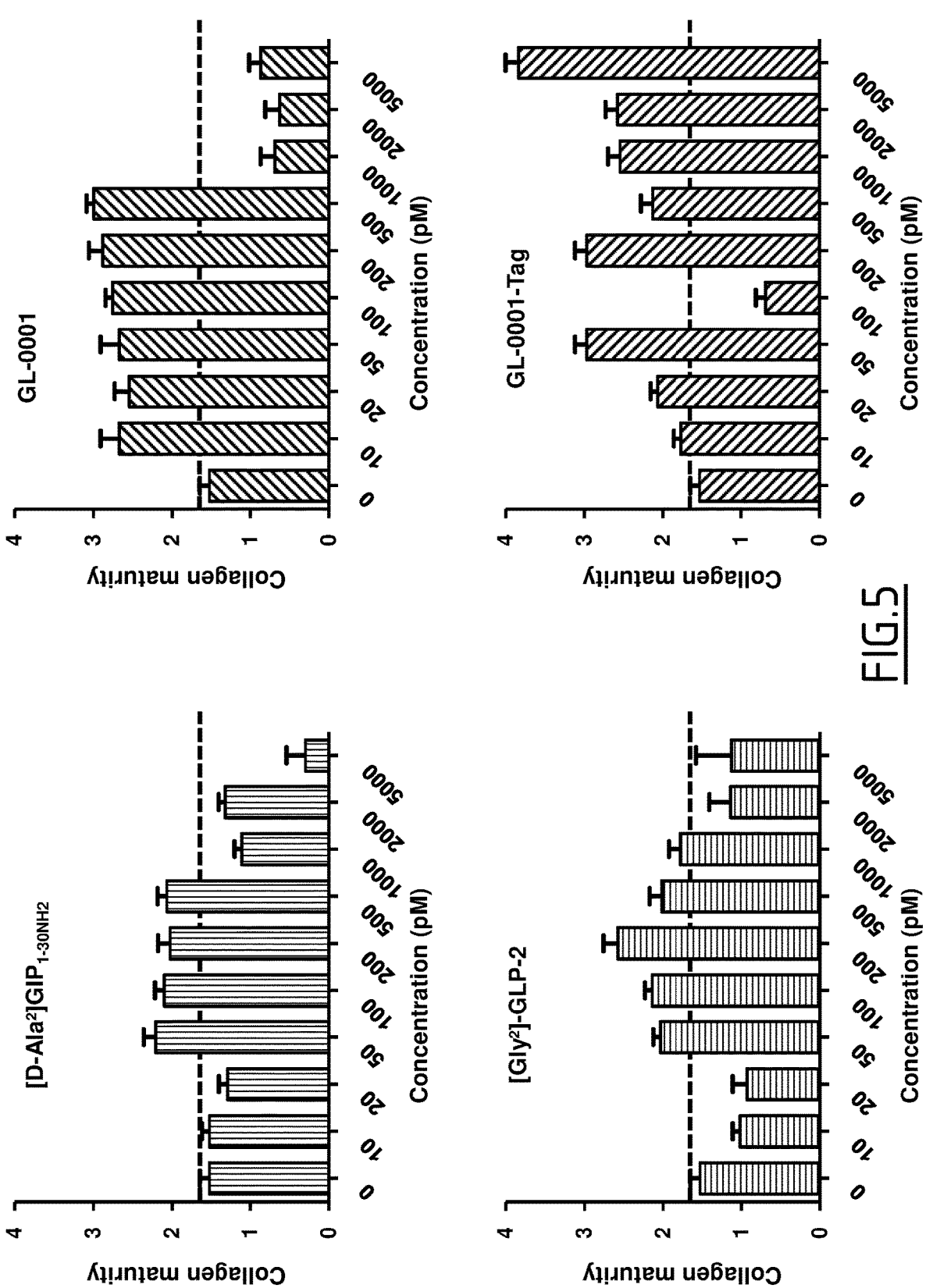
FIGS. 5-7: Effects of double analogue on collagen maturity in vitro. The dotted line corresponds to basal level of collagen maturity.
Figure 6:
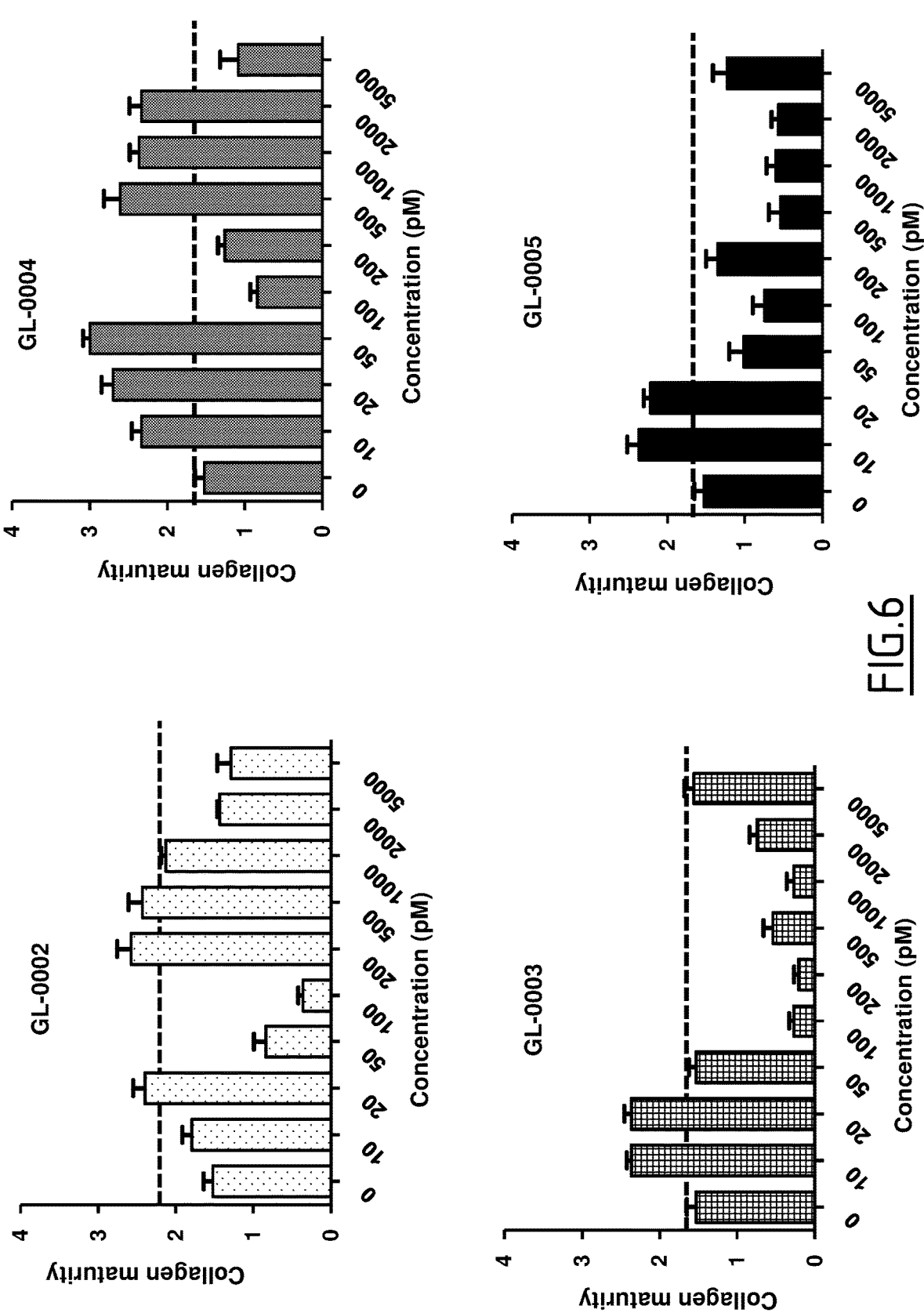
Figure 7:
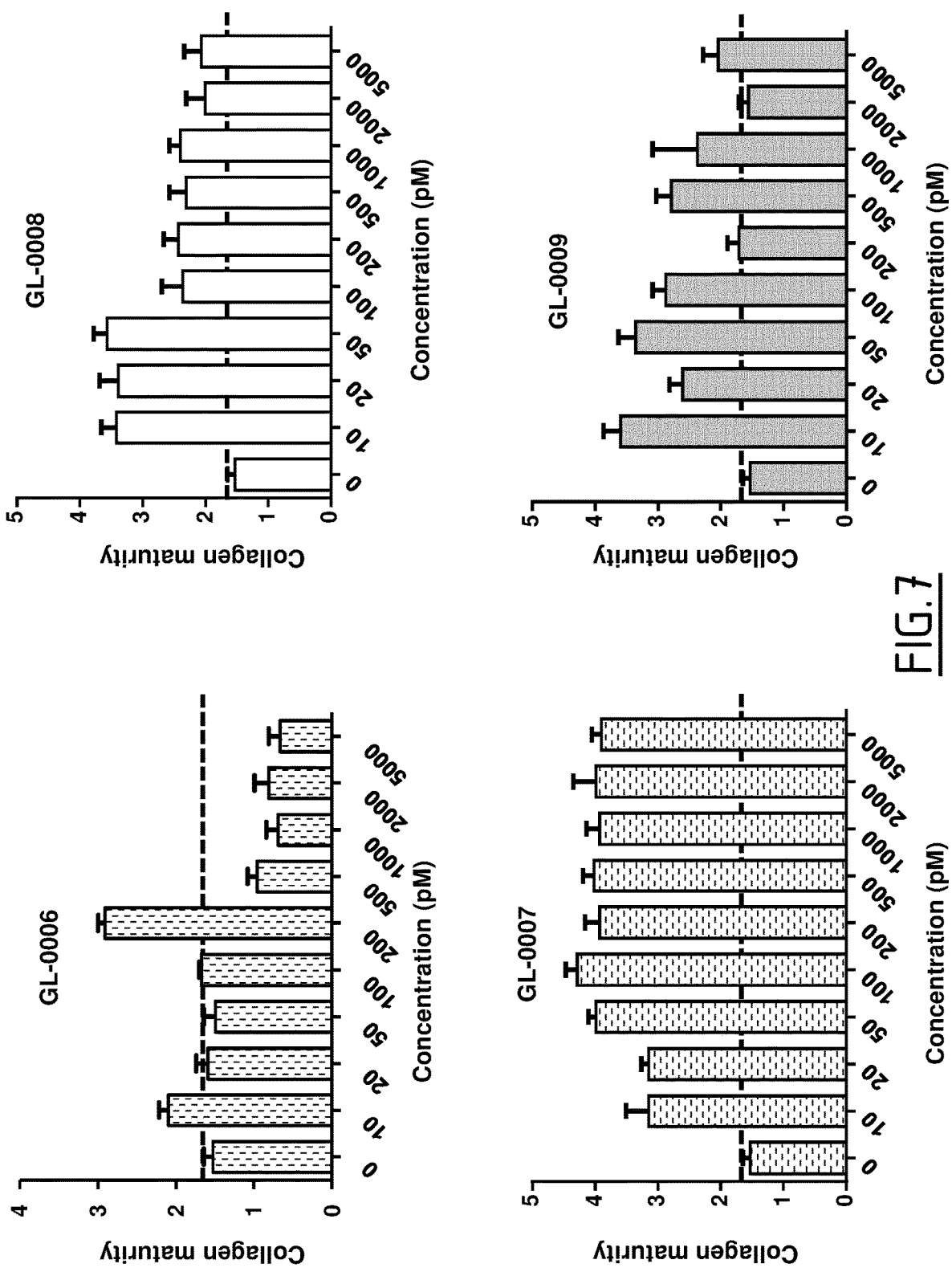

FIGS. 5-7 present the effects of [D-Ala$^2$]-GIP$_{1-30NH2}$, [Gly$^2$]-GLP-2 or the double analogues peptides disclosed in Table 1 on collagen maturity in MC3T3-E1 cultures in vitro. The dotted line corresponds to basal collagen maturity.

Some of the analogues presented with a biphasic profile, namely GL-0001-Tag, GL-0002, GL-0004.

The inventors previously showed that the maximum collagen maturity was obtained at a concentration of 100-200 pM [D-Ala$^2$]GIP$_{1-42}$ (Mieczkowska et al. (2015) *Bone* 74:29-36). As such, the mean collagen maturity between concentrations of 100-200 pM was determined for each analogues and the potency of all these molecules was GL-0007>GL-0001>[Gly$^2$]GLP-2>GL-0008>GL-0006 and GL-0009>[D-Ala$^2$]GIP$_{1-30NH2}$>GL-0001-Tag>GL-0002>GL-0004 and GL-0005>GL-0003.

Although a positive effect was observed with each tested peptide, the inventors identified peptides GL-0001 and GL-0007 as particularly interesting peptides. Based on osteoclast formation in vitro and collagen maturity in vitro, GL-0001 and GL-0007 were the only two peptides with better potency than each native peptide and were thus selected for the following experiments.

7. Effects of GL-0001 or GL-0007 on Body Mass

Figure 8:
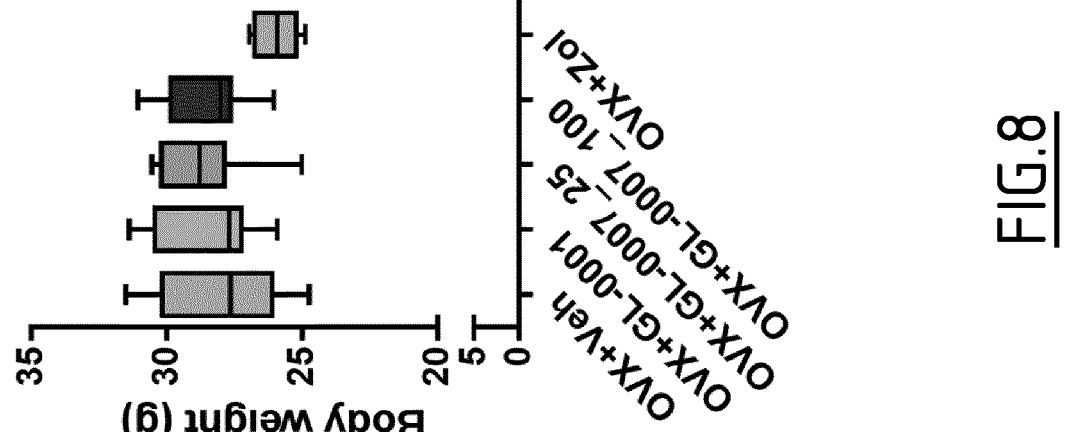
FIG. 8: Effects of GL-0001 or GL-0007 on body mass. Body mass of ovariectomized animals treated with either vehicle (OVX+Veh), 25 nmoles/kg/day GL-0001 (OVX+GL-0001), 25 nmoles/kg/day GL-0007 (OVX+GL-0007_25), 100 nmoles/kg/day GL-0007 (OVX+GL-0007_100) or once 100 µg/kg zoledronic acid (OVX+Zol) are presented at the end of the 8 week treatment. *: p<0.05 and **: p<0.01 vs. OVX+Veh.

FIG. 8 represents the body mass of animals at the end of the 8-week period of treatment. It is worth noting that zoledronic acid-injected animals did not receive any ALZET pump implantation that weight approximately 1.3-1.5 g. As compared with vehicle, none of the treatment led to significant modifications of body weight.

8. Effects of GL-0001 or GL-0007 on Cortical Bone Strength

Figure 9:
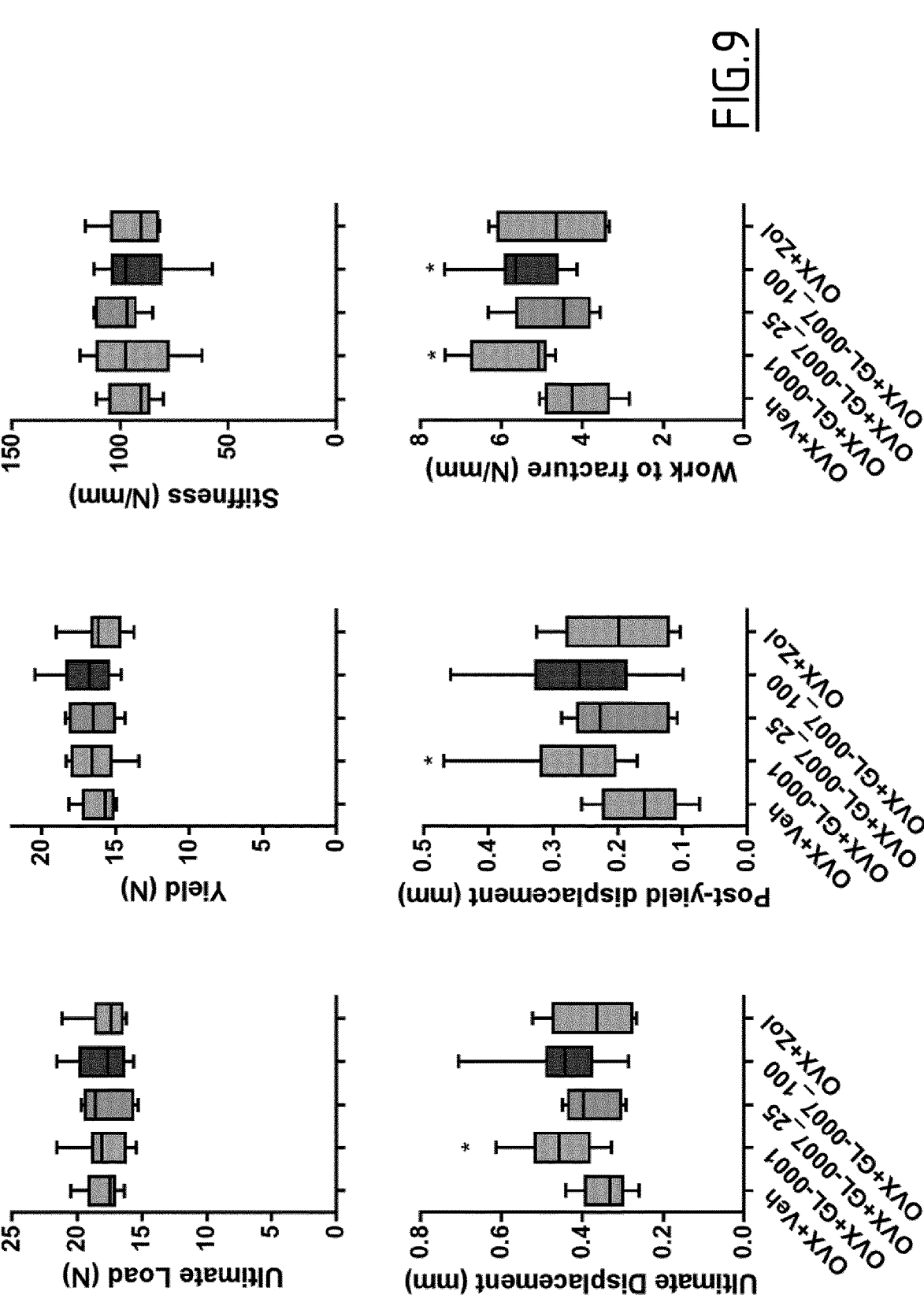
FIG. 9: Effects of GL-0001 or GL-0007 on cortical bone strength. Cortical bone strength was evaluated by 3-point bending assay at the midshaft femur in ovariectomized animals treated with either vehicle (OVX+Veh), 25 nmoles/kg/day GL-0001 (OVX+GL-0001), 25 nmoles/kg/day GL-0007 (OVX+GL-0007_25), 100 nmoles/kg/day GL-0007 (OVX+GL-0007_100) or once 100 µg/kg zoledronic acid (OVX+Zol). *: p<0.05 and **: p<0.01 vs. OVX+Veh.

FIG. 9 presents data on cortical bone strength in the appendicular skeleton in ovariectomy-induced bone loss in mice as a model of post-menopausal osteoporosis. Ovariectomized animals were treated with vehicle, 25 nmoles/kg/day GL-0001, 25 nmoles/kg/day GL-0007 or 100 nmoles/kg/day GL-0007. Zoledronic acid, that represents one of the most used molecules to treat post-menopausal osteoporosis, was used as a positive comparator after a single intravenous administration (100 µg/kg).

Although none of the double analogue or zoledronic acid was potent in modifying ultimate load, yield load or stiffness, GL-0001 was capable of significantly increasing ultimate displacement (34%, p=0.047), post-yield displacement (70%, p=0.038) and work-to-fracture (37%, p=0.022), the latter representing the energy required to break the bone. A higher work-to-fracture means a more resistant bone. GL-0007 at 100 nmoles/kg/day increased ultimate displacement (33%, p=0.054) and post-yield displacement (62%, p=0.074) that ultimately led to a significant augmentation in work-to-fracture (33%, p=0.049).

9. Effects of GL-0001 or GL-0007 on Cortical Bone Microarchitecture.

Figure 10:
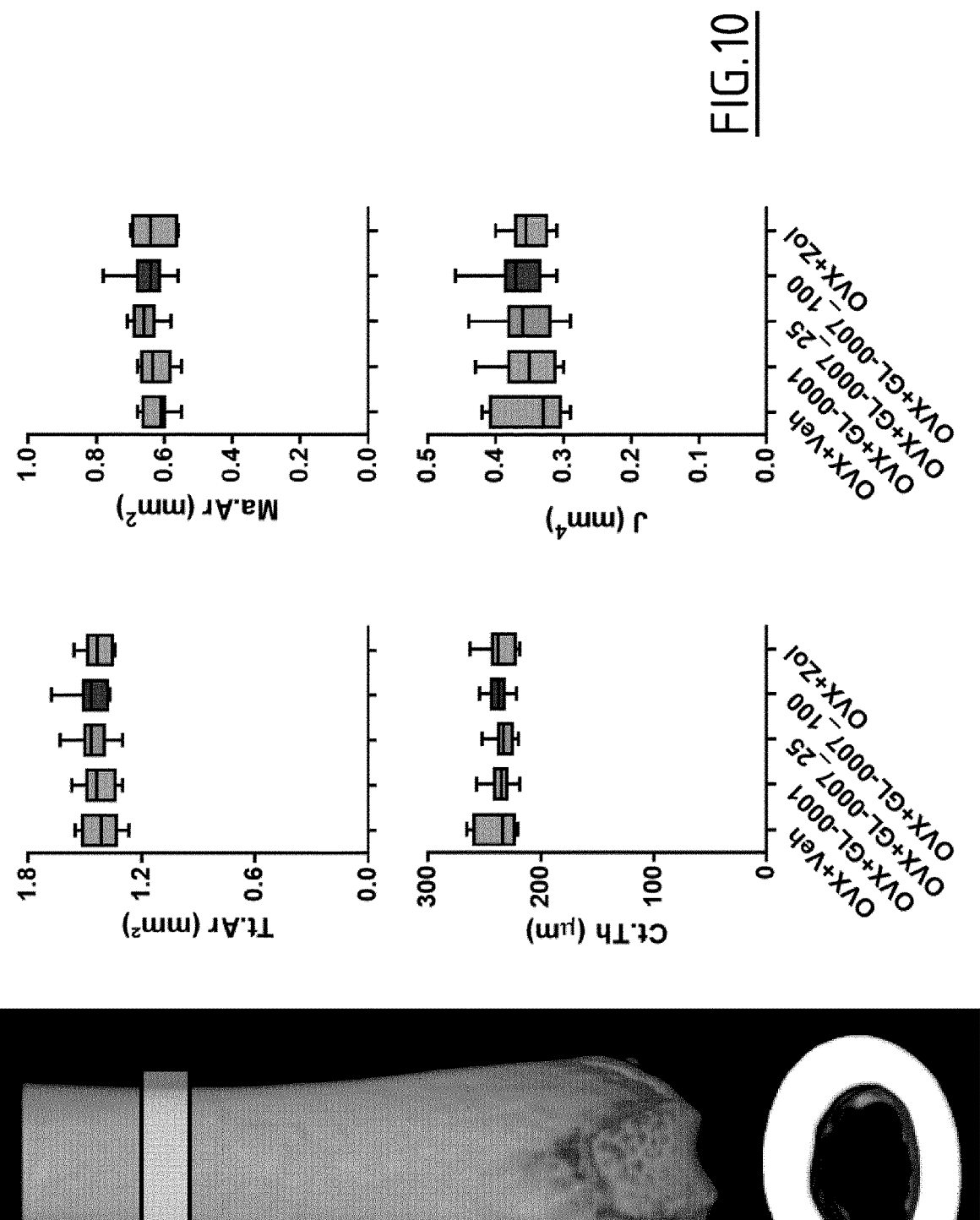
FIGS. 10-11: Effects of GL-0001 or GL-0007 on cortical bone microarchitecture. Cortical bone microarchitecture was evaluated by microcomputed X-ray tomography 4 mm above the distal femur growth plate (white rectangle on 3D model). Animals were either treated with vehicle (OVX+Veh), 25 nmoles/kg/day GL-0001 (OVX+GL-0001), 25 nmoles/kg/day GL-0007 (OVX+GL-0007_25), 100 nmoles/kg/day GL-0007 (OVX+GL-0007_100) or once 100 µg/kg zoledronic acid (OVX+Zol). The studied features were as follows: Tt.Ar: Total cross-sectional area, Ct.Th: cortical thickness, Ma.Ar: medullary area, J: Polar moment of inertia, Ct.Ar: cortical bone area, Ct.Ar/Tt.At: cortical area fraction, Iap: cross-sectional moment of inertia about the antero-posterior axis, Iml: cross-sectional moment of inertia about the medio-lateral axis. *: p<0.05 and **: p<0.01 vs. OVX+Veh.
Figure 11:
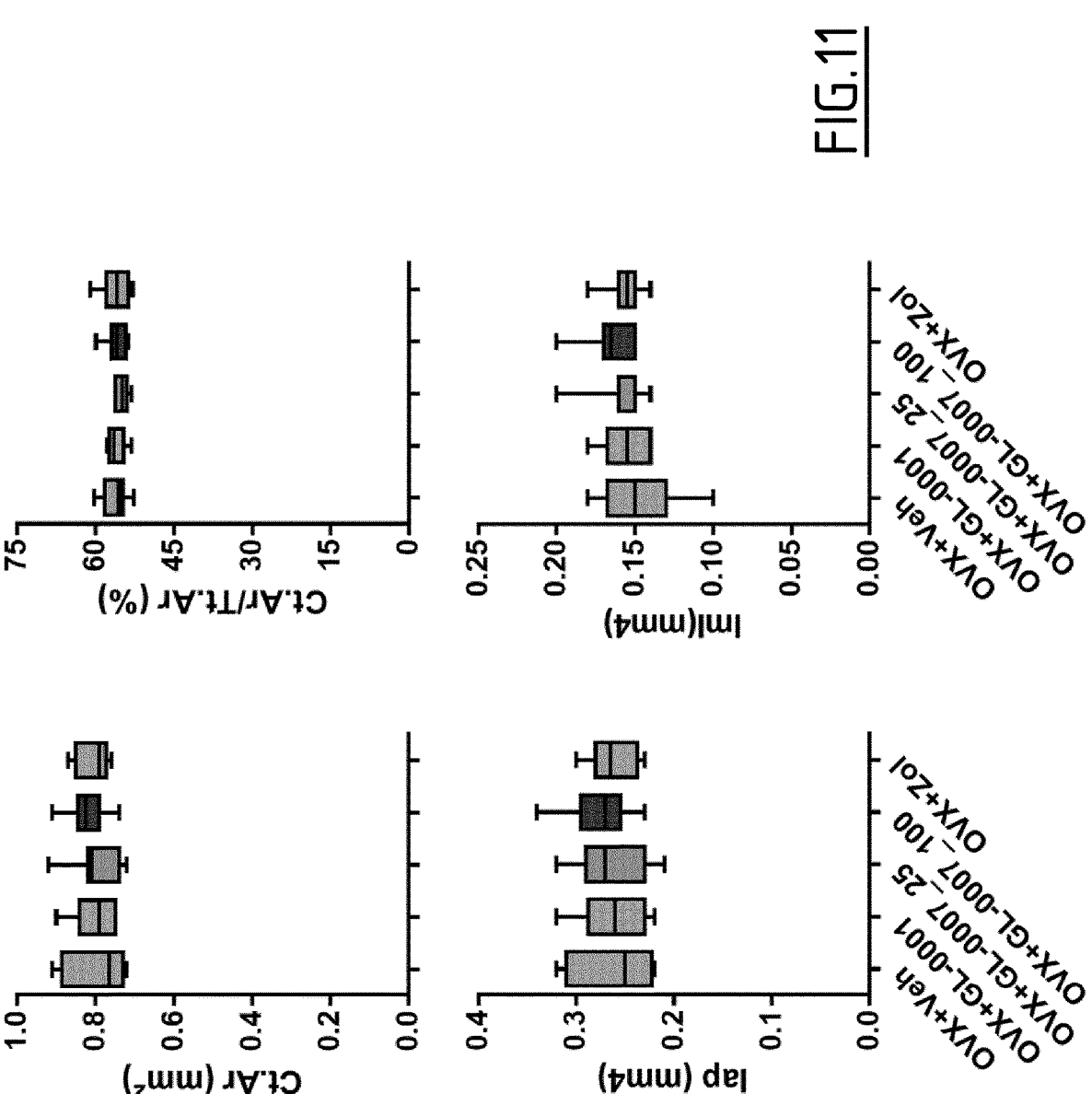

FIGS. 10-11 show data on cortical bone microarchitecture in the appendicular skeleton in ovariectomized mice. Animals were treated with vehicle, 25 nmoles/kg/day GL-0001, 25 nmoles/kg/day GL-0007, 100 nmoles/kg/day GL-0007 or zoledronic acid (once 100 µg/kg iv). Cortical bone microarchitecture was investigated in the femur 4 mm above the distal growth plate. None of the vehicle, double analogues or zoledronic acid were capable of affecting cortical bone microarchitecture.

Figure 12:
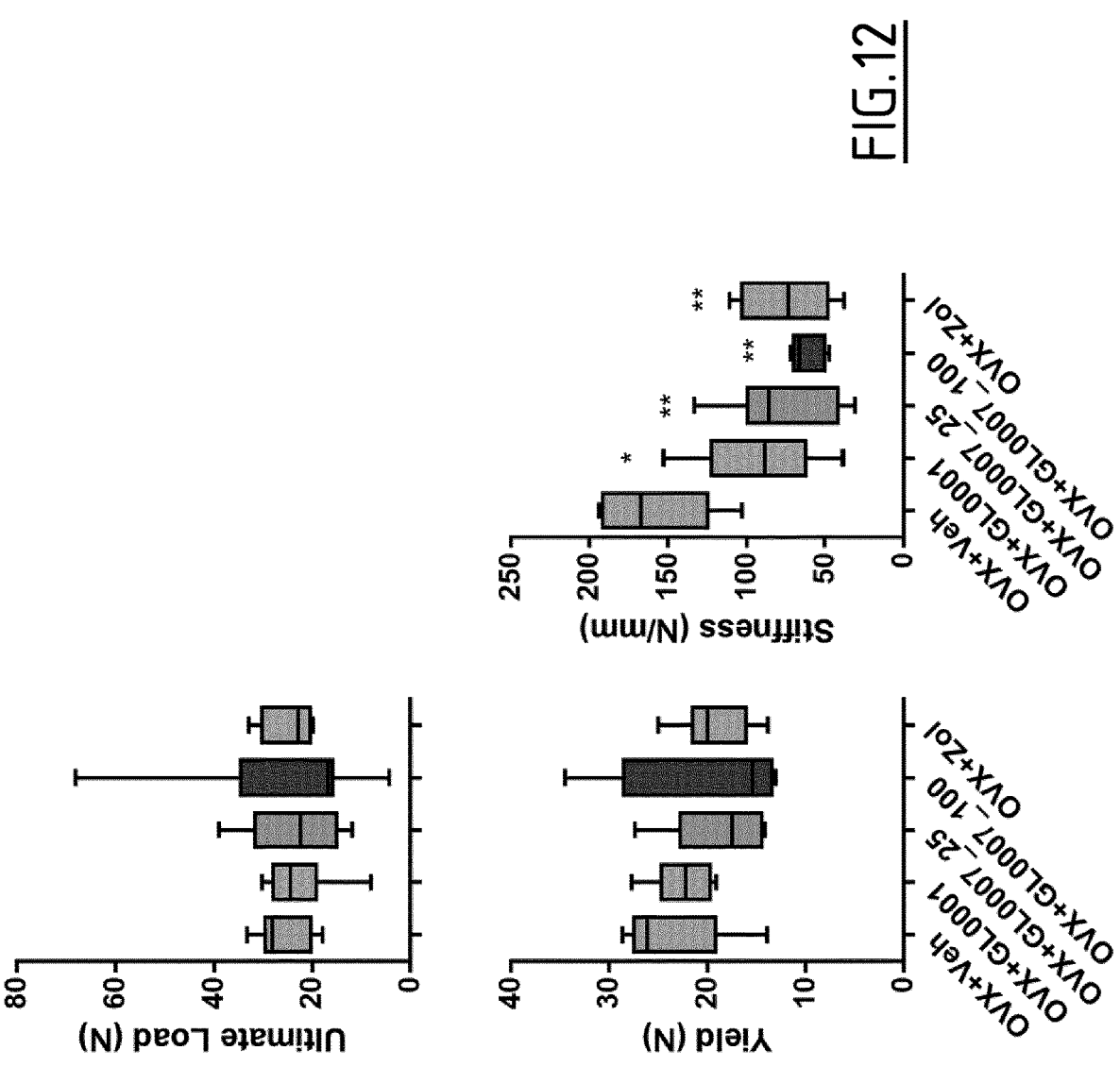
FIGS. 12-13: Effects of GL-0001 or GL-0007 on trabecular bone strength and microarchitecture.
Figure 13:
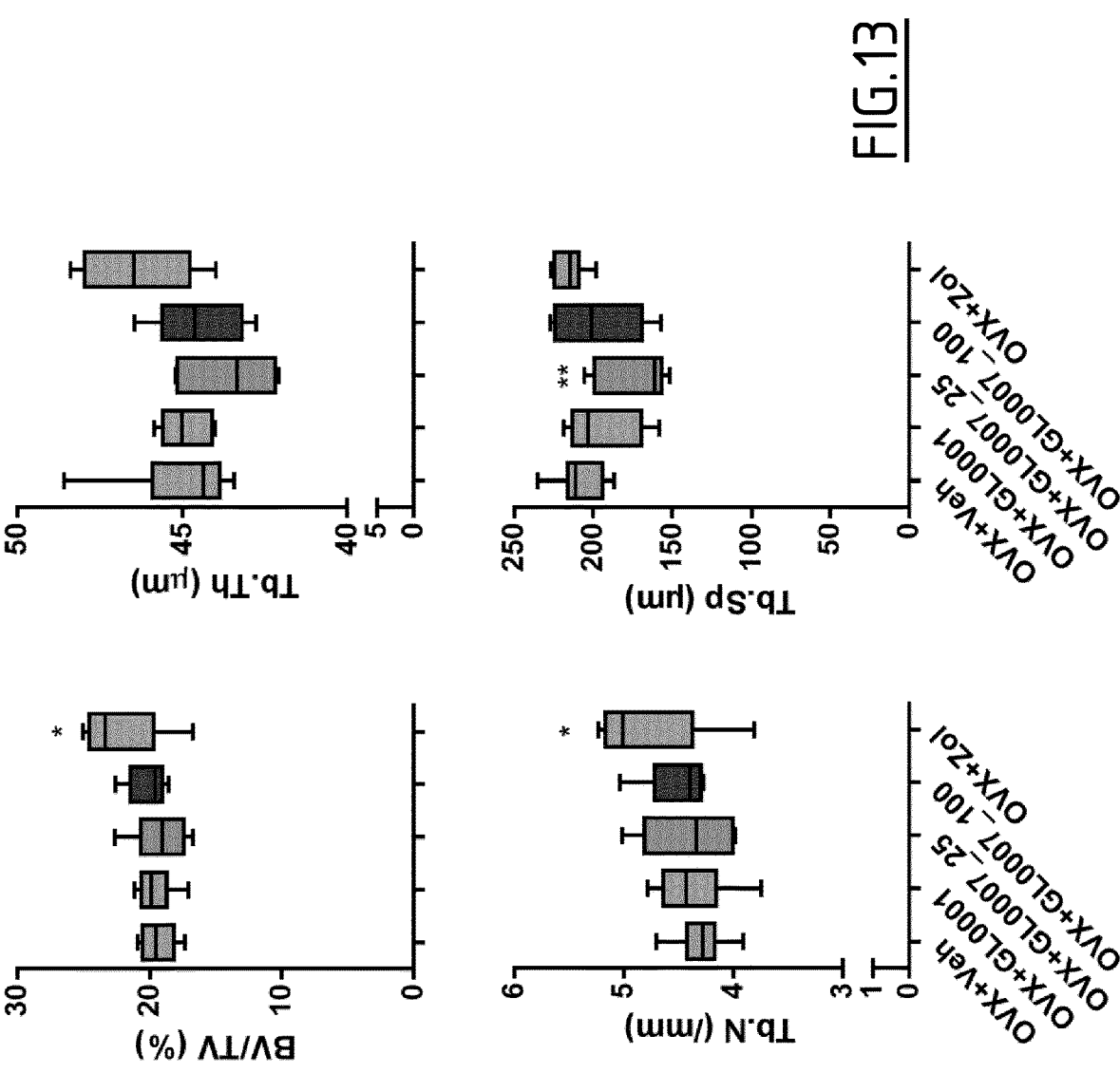

10. Effects of GL-0001 or GL-0007 on Trabecular Bone Strength and Microarchitecture FIGS. 12-13 report data on trabecular bone features in the axial skeleton and more precisely in lumbar spine. Trabecular bone strength was assessed in the second lumbar vertebra by compression test (FIG. 12). As compared to vehicle-treated animals, GL-0001, GL-0007 at both concentrations and zoledronic acid significantly reduced bone stiffness. As compression test is destructive, trabecular microarchitecture was studied in the fifth lumbar vertebra (FIG. 13). As expected, zoledronic acid was capable of increasing trabecular bone mass (BV/TV) by 15% (p=0.013) and trabecular number by 12% (p=0.036). GL-0007 at a concentration of 25 nmoles/kg/day led to a modest but significant (p=0.009) reduction in trabecular spacing by 17%.

11. Effects of GL-0001 or GL-0007 on Bone Matrix Composition

Figure 14:
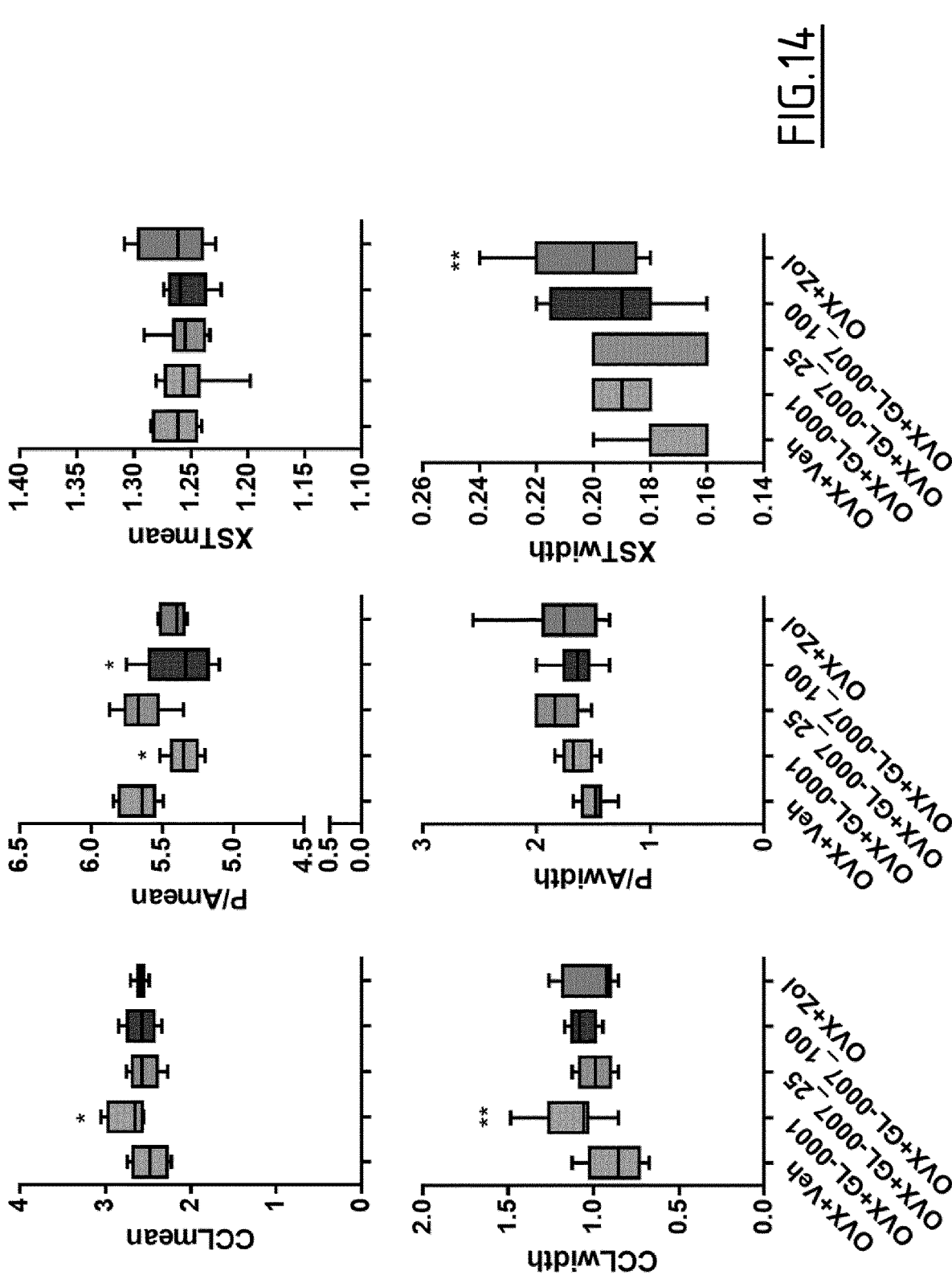
FIGS. 14-15: Effects of GL-0001 or GL-0007 on bone matrix composition. Tissue material properties were evaluated by Fourier transform infrared imaging (FTIRI) in the posterior quadrants at the femur midshaft. Animals were either treated with vehicle (OVX+Veh), 25 nmoles/kg/day GL-0001 (OVX+GL-0001), 25 nmoles/kg/day GL-0007 (OVX+GL-0007_25), 100 nmoles/kg/day GL-0007 (OVX+GL-0007_100) or once 100 µg/kg zoledronic acid (OVX+Zol). CCL: collagen maturity, XST: mineral crystallinity, Crystal_size: crystal size index, P/A: phosphate/amide ratio, C/P: carbonate/phosphate ratio and AcP: acid phosphate content. Mean and heterogeneity (width) of each parameter is represented. *: p<0.05 and **: p<0.01 vs. OVX+Veh.
Figure 15:
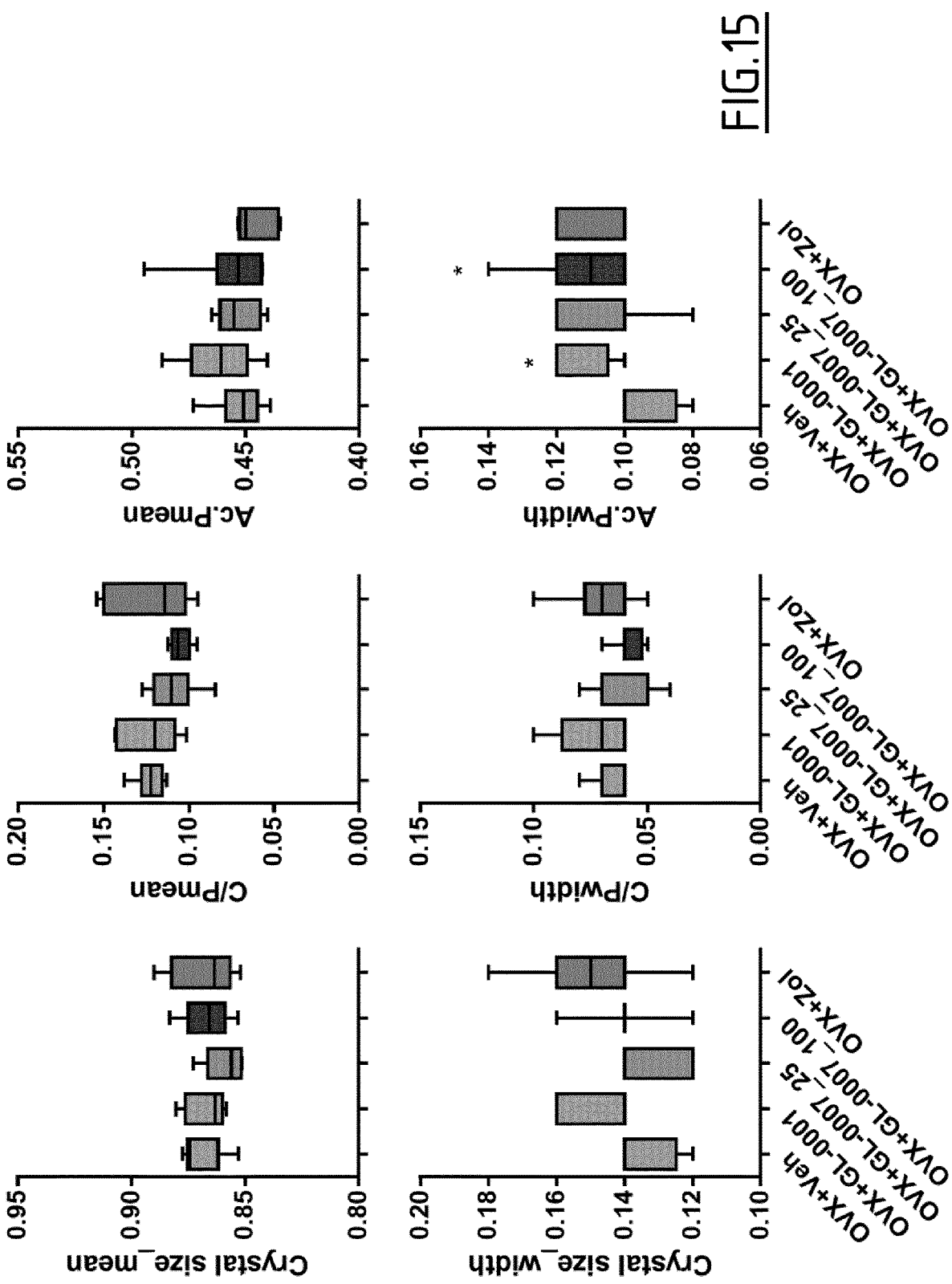

FIGS. 14-15 investigated the effects of double analogue administration on tissue material properties in cortical bone of the appendicular skeleton. As compared with vehicle, GL-0001 significantly increased mean collagen maturity (10%, p=0.017), collagen maturity heterogeneity (28%, p=0.008), acid phosphate content heterogeneity (21%, p=0.016) and reduced mean phosphate/amide ratio (6%, p=0.016). GL-0007 at 100 nmoles/kg/day significantly decreased mean phosphate/amide ratio (5%, p=0.031) and augmented acid phosphate content heterogeneity (18%, p=0.044). Zoledronic acid had modest effects as only mineral crystallinity heterogeneity was significantly augmented (21%, p=0.002).

12. Histological Investigations of Liver and Pancreas Architecture

The inventors performed histological analysis in the liver and the pancreas. Liver and pancreas were processed, embedded, sectioned, stained and examined for any sign of edema, inflammation or necrosis in the presence of vehicle, 25 nmoles/kg/day GL-0001 or 25 nmoles/kg/day GL-0007. No sign of morphological alteration or necrosis were observed between the three groups.

13. Activation of the GIPr and GLP-2r

The inventors studied the rise in cAMP levels in response to vehicle, [D-Ala$^2$]GIP$_{1-30NH2}$, [Gly$^2$]GLP-2 or GL-0001. In HEK 293 cells transfected only with the human GIPr, [D-Ala$^2$]GIP$_{1-30NH2}$ and GL-0001, but not vehicle or [Gly$^2$] GLP-2, increased intracellular levels of cAMP (FIG. 16). In HEK 293 cells transfected only with the human GLP-2r, KITD (SEQ ID NO: 14), peptide Co-7 of sequence HAE-GTFISDYSIAMDKLAARDFINWLIQTKITD (SEQ ID NO: 15) and peptide Co-19 of sequence HADGTFISDYS-TILDNLAARDFINWLIQTKGKK (SEQ ID NO: 16).

Peptides Co-3, Co-7 and Co-19 were cited as double GIP/GLP-2 analogues in WO2018/069442. However, no data were provided for the deposition and maturation of the bone matrix (i.e. collagen maturity) by osteoblasts. This protocol allowed the invention to assess the action of double GIP/GLP-2 analogues as synergic, additive or antagonist.

Materials and Methods

1. Peptide Sequences

All peptides have been made by Fmoc synthesis by GeneCust, Boynes, France. Purity and peptide composition have been verified by high performance liquid chromatography and mass spectrometry. Peptide sequences, lot number and purity are indicated in the table 5 below.

TABLE 5

| Peptides used | | | | |
|---|---|---|---|---|
| Peptide | Sequence | SEQ ID | Lot number | Purity |
| GL-0001 | HGEGSFGSDMSIALDKLAARDFVNWLLQTKITD | 3 | P190228-MJ445040 | 95.41% |
| GL-0007 | HGEGSFGSDFSIALDKLAARDFVNWLLQTK | 4 | P170930-MJ581686 | 99.40% |
| Co-3 | HADGTFISDYSTILDNLAARDFINWLIQTKITD | 14 | P191021-LL755889 | 95.30% |
| Co-7 | HAEGTFISDYSIAMDKLAARDFINWLIQTKITD | 15 | P191021-LL755890 | 96.71% |
| Co-19 | HADGTFISDYSTILDNLAARDFINWLIQTKGKK | 16 | P191021-LL755891 | 95.36% |

[Gly$^2$]GLP-2 and GL-0001, but not vehicle or [D-Ala$^2$] GIP$_{1-30NH2}$, increased intracellular levels of cAMP (FIG. 17). In HEK 293 cells co-transfected with the human GIPr and the human GLP-2r, [D-Ala$^2$]GIP$_{1-30NH2}$, [Gly$^2$]GLP-2 and GL-0001, but not vehicle, increased intracellular levels of cAMP (FIG. 18). It is worth noting that the magnitude of cAMP rise in co-transfected cells was greater with GL-0001 than with each native peptide.

Conclusion

All these data confirm that the peptides of the present invention increase enzymatic cross-linking of collagen matrix produced by osteoblasts at a higher level than each native peptide in vitro and in vivo, reduced the number of generated osteoclasts in a more important way than each native peptide, increased bone resistance to fracture better than the gold standard zoledronic acid and are accordingly potent agents for treating bone disorders

Example 3: Comparison of the Peptides of the Invention with the Peptides of the Prior Art The aim of this study was to compare the potential of double GIP/GLP-2 analogues of the invention, in particular GL-0001 and GL-0007, and three peptides from patent application WO2018/069442, namely peptide Co-3 of sequence HADGTFISDYSTILDNLAARDFINWLIQT- 2. Sequence Homology In order to determine the percentage of homology between the peptide of the invention and peptides disclosed in WO2018/069442, peptide sequences were aligned with the Needleman-Wunsch algorithm in Matlab R2016b (nwalign function).

3. Data

Briefly, MC3T3-E1 subclone 4 cells have been grown and propagated in α-MEM supplemented with 5% fetal bovine serum (FBS), 5% bovine calf serum (BCS), 100 U/mL penicillin, and 100 µg/mL streptomycin in a humidified atmosphere enriched with 5% $CO_2$ at 37° C.

For collagen maturity assay, cells were detached with 0.05% trypsin-EDTA, plated at a density of $1.5 \times 10^4$ cells/cm$^2$ and grown to confluence in α-MEM supplemented with 5% FBS, 5% BCS, 100 U/mL penicillin, and 100 µg/mL streptomycin. At confluence, the culture medium was replaced by the differentiation medium containing α-MEM supplemented with 5% FBS, 5% BCS, 100 U/mL penicillin, 100 µg/mL streptomycin, 50 µg/ml ascorbic acid and various concentrations of GIP, GLP-2 or double GIP/GLP-2 analogues. This day was considered as day 1. The differentiation medium was replenished every two days. At day 14, osteoblast cultures were decellularized by incubation in 0.2 M sodium cacodylate buffer (pH 7.4) containing 0.1% triton X100 for 4 h on an orbital shaker. Cultures were rinsed at least six times with milliQ water, fixed in absolute ethanol, scrapped off the culture dish and transferred onto BaF2 windows where they were air-dried. Integrity of the collagen extracellular matrix was verified by comparing the obtained Fourier transform infrared spectrum with those of commercial collagen. Spectral analysis was performed using a Bruker Vertex 70 spectrometer (Bruker optics, Ettlingen, Germany) interfaced with a Bruker Hyperion 3000 infrared microscope equipped with a standard single element Mercury Cadmium Telluride (MCT) detector. Calibration of the infrared spectrometer is done once a week with a polystyrene film standard (Bruker optics). Infrared spectra were recorded at a resolution of 4 cm$^{-1}$, with an average of 32 scans in transmission mode. Background spectral images were collected under identical conditions from the same BaF2 windows at the beginning and end of each experiment to ensure instrument stability. At least 5 spectra were acquired for each condition and analyzed with a lab-made routine script (version 2.0) in Matlab R2016b (The Mathworks, Natick, MA). The collagen maturity index was determined as the relative ratio of mature trivalent and immature divalent collagen cross-links using their respective subbands located at 1660 cm$^{-1}$ and 1690 cm$^{-1}$ of the amide I peak.

For GIP and GLP-2 dataset, the inventors used the collagen maturity data previously acquired and analyzed.

4. Assessment of Synergism Mode of Action

First of all, collagen maturity obtained in control cultures, i.e. in the absence of double GIP/GLP-2 analogues, were averaged and subtracted to the all dataset. In order to determine the effects of administration of double GIP/GLP-2 analogue, transformed dataset was divided by the mean value of untreated cultures. For each concentration of peptide, the mean, SD and number of events were computed. These data were then exported to GraphPad Prism (version 8.0) for further analysis. The GraphPad Prism analysis consisted in: (1) transformation of drug concentration in log(concentration), (2) curve fitting with either Gaussian, stimulated dose-response (four parameters), sum of two Gaussian or 6$^{th}$ order polynomial function and (3) Estimation of EC50 and E$_{max}$ for each drug.

Furthermore, in order to investigate the synergism effect, the inventors estimated the effects of double GIP/GLP-2 analogues at fixed dose of EC50 encountered with GIP and GLP-2 and of: 0.2, 0.4, 0.8, 0.9, 1.0, 1.2 and 1.5 times EC50 GIP/GLP-2. At each concentration, the combination index was computed using the Chou & Talalay model (Chou & Talalay (1983) *Trends Pharmacol Sci* 4: 450-454) as follows:

$$CI=(E_{GIP}+E_{GLP2}-(E_{GIP} \times E_{GLP2}))/E_{DA}$$

where E$_{GIP}$, E$_{GLP2}$ and E$_{DA}$ represents the effects observed with GIP alone, GLP-2 alone or a dual agonist, respectively. The inventors previously observed that although GIP and GLP-2 exhibited different maximum effects on collagen maturity, their respective EC50 were approximately similar.

5. Statistical Analysis

Differences in combination index at EC50 and 1.5×EC50 were compared with additivity, defined as a value of 1.0±0.15, with a two-tailed t-test. P value <0.05 were considered significant. Data are represented as mean±SD.

Results

1. Sequence Homology Between Peptides of the Invention and Peptides Disclosed WO2018/069442

Percentages of sequence homology have been computerized and presented in Table 6 below. Sequence alignment between GL-0001 and GL-0007, and peptides disclosed in WO2018/069442 are also presented in Table 6 below.

Peptide Co-7 from WO2018/069442 displays the maximum sequence homology with both GL-0001 and GL-0007. As data were provided in WO2018/069442 with peptide Co-3 and Co-19 on alkaline phosphatase, the inventors chose also these two peptides for further comparison.

TABLE 6

Percentage of sequence homology between peptides of the invention and peptides from WO 2018/069442

| | | Peptides of the invention | | | | | | | | | |
| | | GL1 | GL7 | GL2 | GL3 | GL4 | GL5 | GL6 | GL8 | GL9 | GL1t |
|---|---|---|---|---|---|---|---|---|---|---|---|
| Pe | Co1 | 73 | 64 | 64 | 67 | 64 | 64 | 64 | 64 | 64 | 57 |
| | Co2 | 57 | 50 | 50 | 48 | 50 | 50 | 50 | 50 | 50 | 57 |
| | Co3 | 70 | 61 | 61 | 58 | 61 | 61 | 61 | 61 | 61 | 55 |
| | Co4 | 76 | 67 | 67 | 64 | 67 | 67 | 67 | 67 | 67 | 60 |
| | Co5 | 67 | 58 | 58 | 61 | 58 | 58 | 58 | 58 | 58 | 52 |
| | Co6 | 73 | 61 | 64 | 61 | 64 | 61 | 61 | 61 | 61 | 57 |
| | Co7 | 79 | 70 | 67 | 64 | 64 | 64 | 64 | 70 | 70 | 62 |
| | Co8 | 61 | 52 | 52 | 48 | 52 | 52 | 52 | 52 | 52 | 48 |
| | Co9 | 73 | 67 | 67 | 64 | 67 | 67 | 67 | 67 | 67 | 57 |
| | Co10 | 64 | 64 | 64 | 61 | 64 | 64 | 64 | 64 | 64 | 52 |
| | Co11 | 73 | 64 | 64 | 61 | 64 | 64 | 64 | 64 | 64 | 57 |
| | Co12 | 70 | 61 | 61 | 58 | 61 | 61 | 61 | 61 | 61 | 55 |
| | Co13 | 70 | 61 | 61 | 58 | 61 | 61 | 61 | 61 | 61 | 55 |
| | Co14 | 67 | 58 | 58 | 55 | 58 | 58 | 58 | 58 | 58 | 52 |
| | Co15 | 67 | 58 | 58 | 61 | 58 | 58 | 58 | 58 | 58 | 52 |
| | Co16 | 67 | 61 | 61 | 58 | 61 | 61 | 61 | 61 | 61 | 52 |
| | Co17 | 67 | 61 | 61 | 58 | 61 | 61 | 61 | 61 | 61 | 52 |
| | Co18 | 67 | 61 | 61 | 58 | 61 | 61 | 61 | 61 | 61 | 52 |
| | Co19 | 61 | 61 | 61 | 58 | 61 | 61 | 61 | 61 | 61 | 50 |
| | Co20 | 67 | 58 | 58 | 55 | 58 | 58 | 58 | 58 | 58 | 52 |
| | Co24 | 67 | 61 | 61 | 58 | 61 | 61 | 61 | 61 | 61 | 52 |
| | Co25 | 64 | 58 | 58 | 55 | 58 | 58 | 58 | 58 | 58 | 50 |
| | Co26 | 70 | 64 | 64 | 61 | 64 | 64 | 64 | 64 | 64 | 55 |
| | Co27 | 64 | 58 | 58 | 55 | 58 | 58 | 58 | 58 | 58 | 50 |

TABLE 6-continued

Percentage of sequence homology between peptides of the invention and peptides from WO 2018/069442

| | | | | | Peptides of the invention | | | | | | | | | |
| --- | --- | --- | --- | --- | --- | --- | --- | --- | --- | --- | --- | --- | --- | --- |
| | GL1 | GL7 | GL2 | GL3 | GL4 | GL5 | GL6 | GL8 | GL9 | GL1t | | | | |
| Co34 | 52 | 48 | 48 | 45 | 48 | 48 | 48 | 48 | 48 | 48 | Co28 | 64 | 58 | 58 | 58 |

Differences in amino acid composition (identical or same class) at the same position between the peptides of the invention and the peptides of WO2018/069442 peptide has been summarized in FIG. 19.

For GL-0001, major differences with peptide Co-3, Co-7 and Co-19 are at position 7, 12, 13, 31, 32 and 33. For GL-0007, major differences with peptide Co-3, Co-7 and Co-19 are at position 7, 12, 13, 31, 32 and 33.

2. Collagen Maturity as a Function of Peptide Concentration

Figure 20:
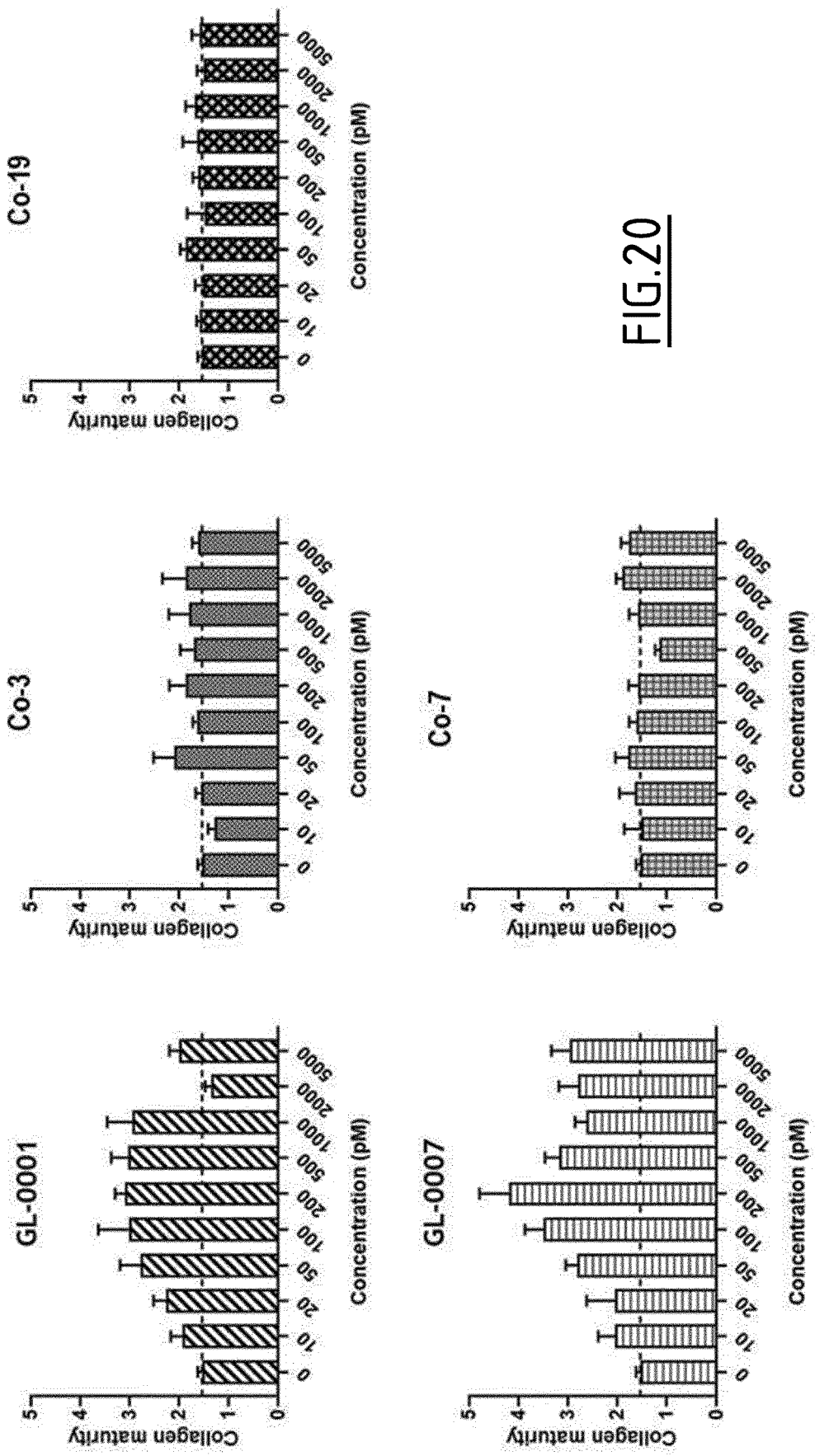
FIG. 20: Collagen maturity index as a function of peptide concentration. Dotted line represents the collagen maturity index observed in cultures without any peptide.

Collagen maturity index obtained as the ratio of trivalent mature/divalent mature collagen crosslinks were measured in the extracellular matrix. FIG. 20 represents the effects of the peptides of the invention and the peptides of WO2018/069442 on this parameter.

As expected, and confirming previous data, GL-0001 and GL-0007 increased collagen maturity above the index observed in the absence of peptide (dotted line). Interestingly, the effects of Peptides Co-3, Co-7 and Co-19 were very modest to raise the collagen maturity index.

3. Dose-Effect Curves of Double GIP/GLP-2 Analogue on Collagen Maturity

Dose-effect curves have been plotted for each double GIP/GLP-2 analogue. The best fit model for each double GIP/GLP-2 analogue is presented in Table 7.

TABLE 7

Estimation of the best fit models for dose-response curve

| Double GIP/GLP-2 analogue | Fit model | $R^2$ |
| --- | --- | --- |
| GL-0001 | Gaussian | 0.647 |
| GL-0007 | Gaussian | 0.590 |
| Co-3 | $6^{th}$ order polynomial | 0.210 |
| Co-7 | $6^{th}$ order polynomial | 0.404 |
| Co-19 | Sum of two gaussian | 0.248 |

4. EC50 of Double GIP/GLP-2 Analogue on Collagen Maturity

EC50 of each double GIP/GLP-2 analogues were identified from dose-effect curves. Reciprocal EC50 are represented in Table 8.

TABLE 8

Determination of EC50 and $E_{max}$ for dose-effect curves. Data represents mean ± SD of 5 individual experiments.

| | Compound | EC50 (pM) | $E_{max}$ (%) |
| --- | --- | --- | --- |
| | [D-Ala$^2$]-GIP$_{1-30}$ | 74 ± 13 | 108.1% |
| | [Gly$^2$]-GLP-2 | 63 ± 42 | 119.3% |
| Invention | GL-0001 | 26.2 ± 17.1 | 207.0% |
| | GL-0007 | 25.9 ± 14.5 | 232.3% |
| WO2018/069442 | Co-3 | 19.4 ± 124.3 | 121.8% |
| | Co-7 | 8.6 ± 6.9 | 115.6% |
| | Co-19 | 22.9 ± 144.3 | 118.1% |

As presented earlier, [D-Ala$^2$]-GIP$_{1-30}$ and [Gly$^2$]-GLP-2 exhibited similar EC50 and hence an average EC50 of 69 pM was used for the determination of combination index. Interestingly, all double GIP/GLP-2 analogues exhibited an EC50 in the same range suggesting that the same concentration can be used to achieve half of the maximum effects. However, clear differences were observed in term of maximum effects ($E_{max}$) as GL-0001 and GL-0007 clearly almost double the maximum effects observed with WO2018/069442 peptides.

5. Combination Index of Double GIP/GLP-2 Analogue on Collagen Maturity

Combination index, based on the Chou & Talalay model, were computed at 0.2, 0.4, 0.8, 0.9, 1.0, 1.2 and 1.5 times mean EC50 of GIP and GLP-2, i.e. at 14, 27, 54, 61, 69, 82 and 100 pM. FIG. 21 represents a plotting of combination indexes over concentration to show the evolution of CI over dose.

Tables 9 and 10 represent the respective combination index of each double GIP/GLP-2 analogues at EC50 and 1.5×EC50.

TABLE 9

Combination index on collagen maturity and their interpretation at EC50

| Compound | CI at EC50 | p value | Interpretation |
| --- | --- | --- | --- |
| GL-0001 | 0.16 ± 0.02 | <0.0001 | Strong synergism |
| GL-0007 | 0.14 ± 0.02 | <0.0001 | Strong synergism |
| Co-3 | 1.29 ± 1.65 | 0.704 | Additive |
| Co-7 | 1.53 ± 1.10 | 0.315 | Additive |
| Co-19 | 277.7 ± 617.4 | 0.346 | Additive |

TABLE 10

Combination index on collagen maturity and their interpretation at 1.5 × EC50

| Compound | CI at 1.5 × EC50 | p value | Interpretation |
| --- | --- | --- | --- |
| GL-0001 | 0.20 ± 0.03 | <0.0001 | Strong synergism |
| GL-0007 | 0.17 ± 0.02 | <0.0001 | Strong synergism |
| Co-3 | 1.79 ± 2.20 | 0.448 | Additive |
| Co-7 | 2.30 ± 1.01 | 0.021 | Antagonism |
| Co-19 | 389.0 ± 864 | 0.345 | Additive |

CI>10: very strong antagonism; CI 3.3-10: strong antagonism; CI 1.45-3.3: antagonism; CI 1.15-1.45 moderate antagonism; CI 0.85-1.15: additive; CI 0.85-0.65: moderate synergism; CI 0.3-0.65: synergism; CI 0.1-0.3 strong synergism; CI<0.1: very strong synergism.

Data are presented as mean±SD of 5-13 experiments. Two-tailed t-test have been used to assess whether CI were significantly different as compared with additivity (1.0±0.15).

GL-0001 and GL-0007 displayed, at 69 pM and 100 pM, combination indexes suggesting strong synergism. Previously, the inventors already exhibited similar behavior with combination index for GL-0001 and GL-0007 supporting of synergism. The present study is in adequation with previous obtained data.

Interestingly, none of peptides Co-3, Co-7 and Co-19 presented synergism properties but rather additive or antagonism depending on the concentration.

Based on combination index at EC50 and 1.5×EC50, only GL-0001 and GL-0007 appears as good candidate for synergism.

Conclusions

This study compared the effects of double GIP/GLP-2 analogues of the invention and peptides disclosed in the WO2018/069442 patent application.

GL-0001 and GL-0007, which are peptides of the invention, were selected as they represent the best compromise in term of action on collagen maturity and osteoclastogenesis. Sequence alignment with WO2018/069442 peptides showed that peptide Co-7 was the closest peptide to GL-0001 and GL-0007. As data on alkaline phosphatase were provided in WO2018/069442 with peptide Co-3 and peptide Co-19, the inventors decided to compare head-to-head the action of GL-0001 and GL-0007 in one hand, to peptides Co-3, Co-7 and Co-19, in the other hand. Although all peptides exhibited a similar EC50, clear differences were evident in the magnitude of the maximum effects. This implies that for the same dose of peptide, the effects on collagen maturity would be greater with the peptides of the invention. Furthermore, the pharmacological mechanisms behind double GIP/GLP-2 analogues were deciphered and whilst the peptides of the invention presented a strong synergism, WO2018/069442 peptides showed additive or antagonism mode of action.

Example 4: Comparison of the Peptides of the Invention with the Peptides of the Prior Art The aim of this study was to compare the potential of double GIP/GLP-2 analogues of the invention, namely GL-0001 and GL-0007, and three peptides from patent application WO2018/069442, namely peptides Co-3, Co-7 and Co-19 on osteoclastogenesis in vitro.

Materials and Methods

1. Peptide Sequences
Peptides were as disclosed in Example 3.
2. Cells and Propagation Method
Murine Raw 264.7 cells were grown and expanded in propagation medium containing Dulbecco's modified Eagle medium (DMEM—Gibco) supplemented with 10% fetal bovine serum (FBS—Lonza), 100 U/mL penicillin and 100 µg/mL streptomycin (Gibco) in a humidified atmosphere enriched with 5% $CO_2$ at 37° C. The first passage after thawing Raw 264.7 cells was considered as passage 1. Cells were used up to passage 8.
3. Osteoclastogenesis Assay
Murine Raw 264.7 cells were scrapped off the plastic dish, plated at a density of $1.25×10^4$ cells/cm$^2$ and grown in propagation medium enriched with 10 ng/ml soluble murine RANKL (Bio-Techne, ref 462-TEC-010). After 110 h, cells were fixed with formalin (10% in PBS buffer) for 10 min and rinsed in distilled water prior to tartrate resistant acid phosphatase (TRAcP) staining.

TRAcP was histochemically revealed by a simultaneous coupling reaction using Naphtol AS-BI-phosphate (Sigma Aldrich) as substrate and Fast violet B (Sigma-Aldrich) as the diazonium salt for 90 min at 37° C. in the dark. Cultures were rinsed three times in distilled water and the residual activity was inhibited by 4% NaF (Sigma-Aldrich) for 30 min. Cells were then rinsed in distilled water and allowed to dry. TRAcP positive cells, with more than three nuclei, were identified as osteoclasts. The number of newly generated osteoclasts was assessed using light microscopic examination by a histologist that was blinded to the treatment intervention. Dataset acquired previously with (D-Ala$^2$) GIP$_{1-30}$ and (Gly$^2$)GLP-2 were used in the present example for comparison and combination index computation.
4. Evaluation of Data
Osteoclast numbers obtained with double GIP/GLP-2 analogues were first reported as percentage of osteoclast numbers observed in the absence of peptides (RANKL alone). For each concentration of peptide, the mean, SD and number of events were computed. These data were then exported to GraphPad Prism (version 8.0) for further analysis. The GraphPad Prism analysis consisted in: (1) transformation of drug concentration in log(concentration), (2) curve fitting with 3 parameter Log(inhibitor) vs. response model (top constrain to 100) and (3) Estimation of IC50 for each drug.

Furthermore, in order to investigate the synergism effect, the inventors converted the osteoclastogenesis data into the inhibitory effect by subtracting each osteoclastogenesis percentage to 100. These data were then exported to GraphPad Prism were the analysis consisted in (1) transformation of drug concentration in log(concentration), (2) curve fitting with 3 parameter Log(agonist) vs. response model (bottom constrain to 0) and (3) estimation of EC50 and $E_{max}$ for each drug. The effects of double GIP/GLP-2 analogues at EC50 encountered with GIP and GLP-2 (36.8 pM) was used from previous conducted experiments and combination indexes were computed according to Chou & Talalay (Chou & Talalay (1983) *Trends Pharmacol Sci* 4: 450-454) as follows:

$$CI=(E_{GIP}+E_{GLP2}-(E_{GIP}×E_{GLP2}))/E_{DA}$$

where $E_{GIP}$, $E_{GLP2}$ and $E_{DA}$ represents the effects observed with GIP alone, GLP-2 alone or a dual agonist, respectively.

Results

Figure 22:
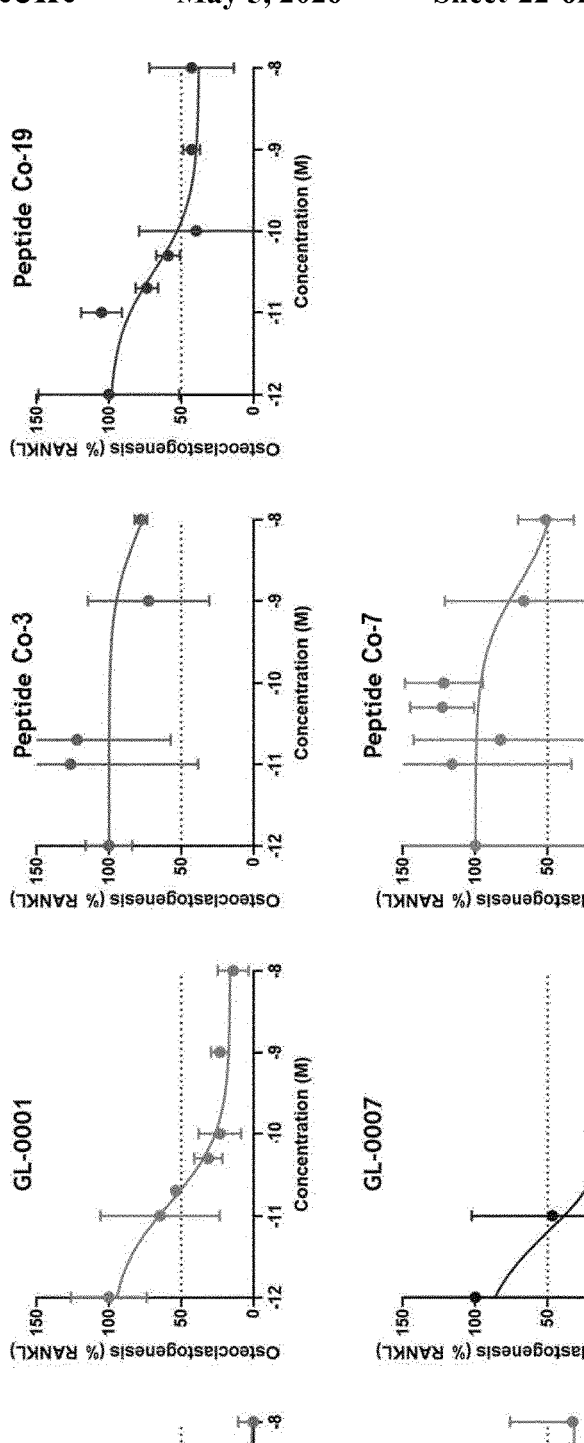
FIG. 22: Osteoclastogenesis response of Raw 264.7 cells exposed to several concentrations of double GIP/GLP-2 analogues. The dashed line represents half maximum effects used to compute IC50.

1. Osteoclastogenesis
All peptides reduced the amount of newly generated osteoclasts at the highest concentration. Curve fitting of osteoclast response is presented in FIG. 22 for all peptides. IC50 was deduced from curve fitting and presented in Table 11.

TABLE 11

IC50 computed from curve fitting of osteoclastogenesis vs. peptide concentration.

| | Peptide | IC50 |
|---|---|---|
| | (D-Ala$^2$)GIP$_{1-30}$ | 41.4* |
| | (Gly$^2$)GLP-2 | 32.2* |
| Invention | GL-0001 | 14.2 |
| | GL-0007 | 6.2 |
| WO2018/069442 | Co-3 | ND |
| | Co-7 | 1475 |
| | Co-19 | 32.4 |

ND: Not determined as the maximum effects did not reach 50% inhibition.
*determined from previous experiments.

Interestingly, (D-Ala$^2$)GIP$_{1-30}$ and (Gly$^2$)GLP-2 presented similar IC50. A two-tailed t-test confirmed this finding. As such, an intermediate IC50 of 36.8 pM was used to investigate the "synergism" properties of double GIP/GLP-2 analogues.

2. Dose-Response Inhibitory Effect of Double GIP/GLP-2 Analogue on Osteoclastogenesis and Pharmacological Mechanism In order to evaluate the response of each double GIP/GLP-2 analogues, the inventors transformed the data as a percentage of inhibition of osteoclastogenesis. Data were then curve fitted and $R^2$ value of each curve fitting is presented in table 12.

TABLE 12

Estimation of the best fit models for dose-response curve

| | Peptide | $R^2$ |
|---|---|---|
| | $(D-Ala^2)GIP_{1-30}$ | 0.835 |
| | $(Gly^2)GLP-2$ | 0.541 |
| Invention | GL-0001 | 0.781 |
| | GL-0007 | 0.363 |
| WO2018/069442 | Co-3 | 0.173 |
| | Co-7 | 0.185 |
| | Co-19 | 0.552 |

Figure 23:
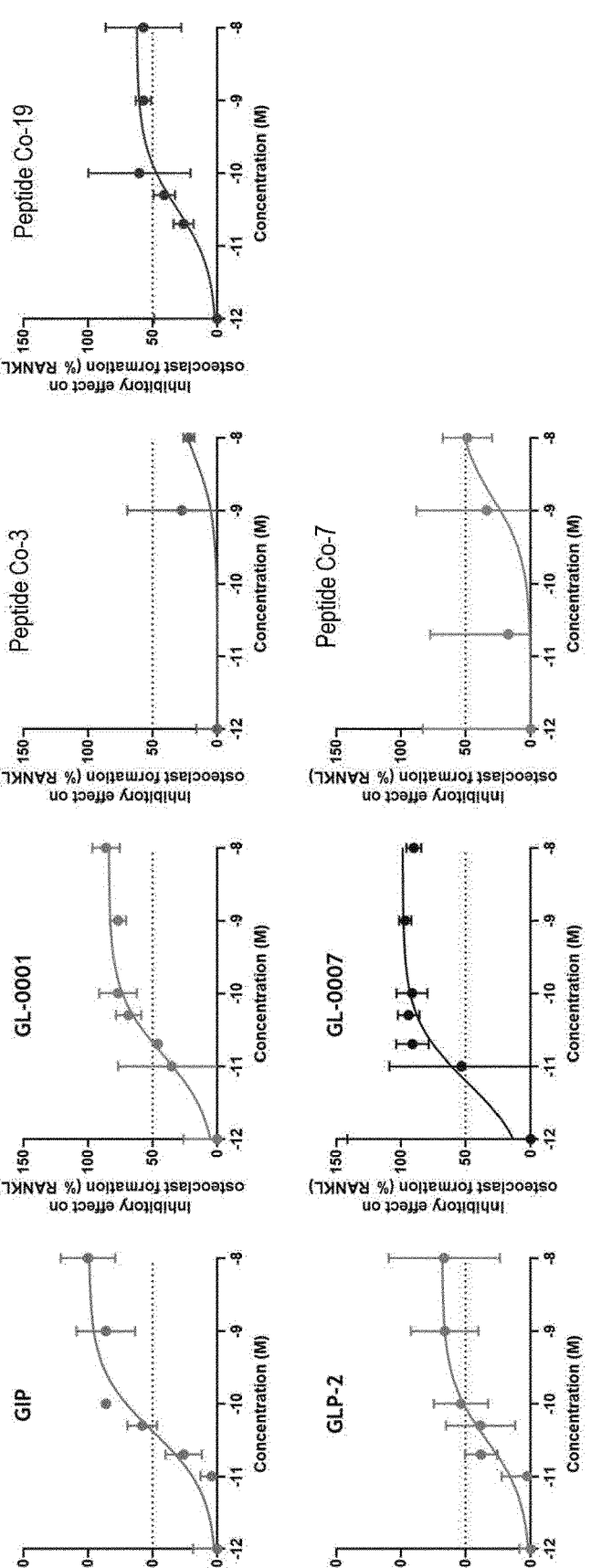
FIG. 23: Dose response of inhibitory effects of double GIP/GLP-2 analogues. The dashed line represents half maximum effects (EC50).

Dose-effect curves have been plotted for each double GIP/GLP-2 analogue and are presented FIG. 23. EC50 and maximum inhibitory effect ($E_{max}$) have been computed for each double GIP/GLP-2 analogues and are represented in Table 13.

TABLE 13

Determination of EC50 and $E_{max}$ for dose-effect curves.

| | Compound | $EC_{50}$ (pM) | $E_{max}$ (%) |
|---|---|---|---|
| | $(D-Ala^2)GIP_{1-30}$ | 41.4* | 99.51* |
| | $(Gly^2)GLP-2$ | 32.2* | 68.12* |
| Invention | GL-0001 | 14.2 | 83.96 |
| | GL-0007 | 6.2 | 98.64 |
| WO2018/069442 | Co-3 | ND | 37.88 |
| | Co-7 | 1475 | 58.05 |
| | Co-19 | 32.4 | 62.36 |

Data represents mean ± SD of 5 individual experiments.
*data obtained in previous experiments.

It appeared interesting to determine whether the osteoclast response observed with double GIP/GLP-2 analogues is equal, higher or lower than the joint administration of both $(D-Ala^2)GIP_{1-30}$ and $(Gly^2)GLP-2$. To answer this question, combination index, according to Chou & Talalay, have been

Figure 24:
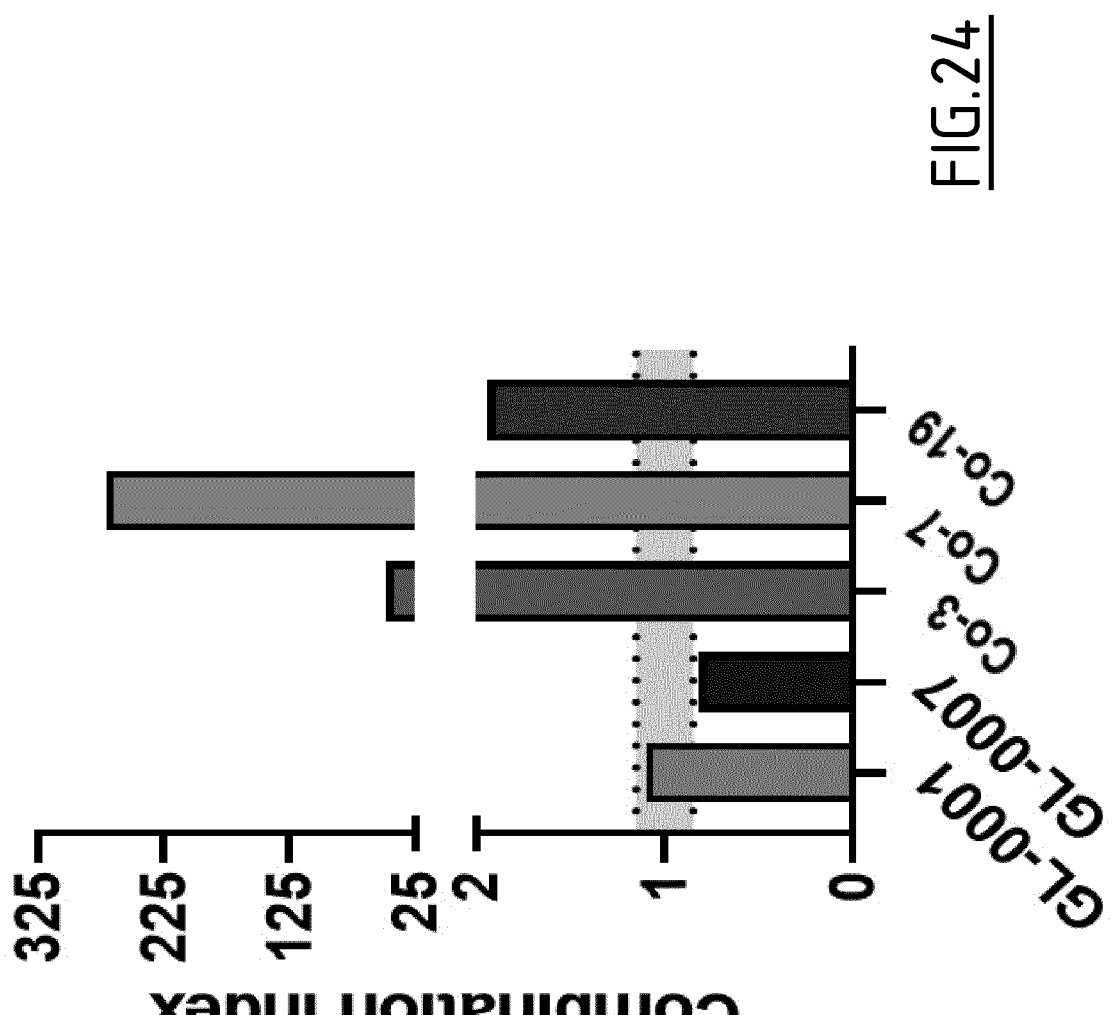
FIG. 24: Combination index (CI) at EC50 of GIP and GLP-2 for osteoclastogenesis. Grey area between dashed lines represents CI values indicative of additivity. Values above grey area are suggestive of antagonism whilst values below grey area are indicative of synergism.

34 computed and are reported in Table 14. Furthermore, Combination index at $EC_{50}$ of $(D-Ala^2)GIP_{1-30}$ and $(Gly^2)GLP-2$ have been plotted in FIG. 24.

TABLE 14

Combination index at EC50 of GIP and GLP-2 and pharmacological interpretation

| Compound | CI at EC50 | Interpretation |
|---|---|---|
| GL-0001 | 1.10 | Additive |
| GL-0007 | 0.82 | Moderate synergism |
| Co-3 | 48.00 | Very strong antagonism |
| Co-7 | 271.28 | Very strong antagonism |
| Co-19 | 1.94 | Antagonism |

CI>10: very strong antagonism; CI 3.3-10: strong antagonism; CI 1.45-3.3: antagonism; CI 1.15-1.45 moderate antagonism; CI 0.85-1.15: additive; CI 0.85-0.65: moderate synergism; CI 0.3-0.65: synergism; CI 0.1-0.3 strong synergism; CI<0.1: very strong synergism.

Two-tailed t-test have been used to assess whether CI were significantly different as compared with additivity (1.0±0.15).

Conclusions

This study shows that peptides of the invention, in particular GL-0001 and GL-0007, presented an EC50 lower than peptides of the prior art. This suggest that lower doses of GL-0001 and GL-0007 can be used to achieve 50% inhibition in osteoclast formation. Furthermore, $E_{max}$ values for GL-0001 and GL-0007 indicated that both peptides achieved more than 85% inhibition of osteoclast formation, which is higher than $(Gly^2)GLP-2$ alone. The pharmacological mechanisms behind GL-0001 and GL-0007 effects range from moderate synergism to additive. Interestingly, peptides disclosed in WO2018/069442, namely peptides Co-3, Co-7 and Co-19, presented equal or higher EC50, as compared with $(D-Ala^2)GIP_{1-30}$ or $(Gly^2)GLP-2$ alone, suggesting that the same dose or even higher doses are required to inhibit 50% of osteoclast formation. Furthermore, the highest inhibitory effects encountered with these three peptides was at best ~62.4%, which is lower than effects observed with $(Gly^2)GLP-2$ or $(D-Ala^2)GIP_{1-30}$ alone. Furthermore, the pharmacological mode of action of these three peptides ranged from antagonism to very strong antagonism.

The invention claimed is:

1. An isolated peptide comprising the consensus amino acid sequence SEQ ID NO: 1:

```
                                    (SEQ ID NO: 1)
HGEGSFX₇SDX₁₀ SX₁₂X₁₃LDKLAARDFVNWLLQTK
``` wherein $X_7$ is an amino acid selected from the group consisting in glycine, valine, and threonine, $X_{10}$ is an amino acid residue selected from the group consisting of methionine, leucine and phenylalanine, $X_{12}$ is an amino acid selected from the group consisting in isoleucine and valine and $X_{13}$ is an amino acid selected from the group consisting in alanine and valine, provided that when $X_{12}$ is isoleucine, then $X_{13}$ is alanine, and when $X_{12}$ is valine, $X_{13}$ is valine.

2. The peptide according to claim 1, wherein the C-terminal lysine is amidated.

3. The peptide according to claim 1, comprising the consensus amino acid sequence SEQ ID NO: 2:

```
                                    (SEQ ID NO: 2)
HGEGSFX₇SDX₁₀ SX₁₂X₁₃LDKLAARDFVNWLLQTKITD,
``` wherein $X_7$ is an amino acid selected from the group consisting in glycine, valine, and threonine, $X_{10}$ is an amino acid residue selected from the group consisting of methionine, leucine and phenylalanine, $X_{12}$ is an amino acid selected from the group consisting in isoleucine and valine and $X_{13}$ is an amino acid selected from the group consisting in alanine and valine, provided that when $X_{12}$ is isoleucine, then $X_{13}$ is alanine, and when $X_{12}$ is valine, $X_{13}$ is valine.

4. The peptide according to claim 3, further comprising a peptide tag at its C-terminal end.

5. An isolated peptide comprising an amino acid sequence selected from the group consisting of the peptides:

```
GL-0001 of sequence
                                    (SEQ ID NO: 3)
HGEGSFGSDMSIALDKLAARDFVNWLLQTKITD, GL-0007 of sequence
                                    (SEQ ID NO: 4)
HGEGSFGSDFSIALDKLAARDFVNWLLQTK-NH₂,
```

-continued

```
GL-0001-Tag of sequence
                                    (SEQ ID NO: 5)
HGEGSFGSDMSIALDKLAARDFVNWLLQTKITDGAADDDDDD, GL-0004 of sequence
                                    (SEQ ID NO: 8)
HGEGSFVSDMSVVLDKLAARDFVNWLLQTK-NH₂, GL-0005 of sequence
                                    (SEQ ID NO: 9)
HGEGSFVSDLSVVLDKLAARDFVNWLLQTK-NH₂, GL-0006 of sequence
                                    (SEQ ID NO: 10)
HGEGSFVSDFSVVLDKLAARDFVNWLLQTK-NH₂, and GL-0008 of sequence
                                    (SEQ ID NO: 11)
HGEGSFTSDFSIALDKLAARDFVNWLLQTK-NH₂.
```

6. A pharmaceutical composition comprising a peptide as defined in claim 1.

7. An implantable medical device comprising a peptide as defined in claim 1.

8. A bone filling biomaterial comprising a peptide as defined in claim 1.

9. A method for treating a bone disorder in a subject, comprising administering to a subject in need thereof a therapeutically effective amount of a peptide as defined in claim 1, wherein the bone disorder is selected from osteoporosis, osteopenia, diabetic bone disease, osteomalacia, rickets, and bone dystrophies.

10. The method according to claim 9, wherein the bone dystrophies are Paget's disease of bone, osteogenesis imperfecta, and osteomyelitis.

11. The method according to claim 10, wherein said bone disorder is osteogenesis imperfecta.

12. A method for treating a bone disorder in a subject, comprising administering to the subject a therapeutically effective amount of a pharmaceutical composition as defined in claim 6, wherein the bone disorder is selected from osteoporosis, osteopenia, diabetic bone disease, osteomalacia, rickets, and bone dystrophies.

13. The method according to claim 12, wherein the bone dystrophies are Paget's disease of bone, osteogenesis imperfecta, and osteomyelitis.

14. The method according to claim 13, wherein said bone disorder is osteogenesis imperfecta.

* * * * *

SEQUENCE LISTING

```
<160> NUMBER OF SEQ ID NOS: 16

<210> SEQ ID NO 1
<211> LENGTH: 30
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (7)..(7)
<223> OTHER INFORMATION: Xaa = any amino acid residue
<220> FEATURE:
<221> NAME/KEY: MISC_FEATURE
<222> LOCATION: (10)..(10)
<223> OTHER INFORMATION: Xaa = any amino acid residue
<220> FEATURE:
<221> NAME/KEY: MISC_FEATURE
<222> LOCATION: (12)..(12)
<223> OTHER INFORMATION: Xaa = any amino acid residue
```

```
<220> FEATURE:
<221> NAME/KEY: MISC_FEATURE
<222> LOCATION: (13)..(13)
<223> OTHER INFORMATION: Xaa = any amino acid residue

<400> SEQUENCE: 1

His Gly Glu Gly Ser Phe Xaa Ser Asp Xaa Ser Xaa Xaa Leu Asp Lys
1               5                   10                  15

Leu Ala Ala Arg Asp Phe Val Asn Trp Leu Leu Gln Thr Lys
            20                  25                  30

<210> SEQ ID NO 2
<211> LENGTH: 33
<212> TYPE: PRT
<213> ORGANISM: Artificial Sequence
<220> FEATURE:
<223> OTHER INFORMATION: Longer consensus sequence
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid

<400> SEQUENCE: 2

His Gly Glu Gly Ser Phe Xaa Ser Asp Xaa Ser Xaa Xaa Leu Asp Lys
1               5                   10                  15

Leu Ala Ala Arg Asp Phe Val Asn Trp Leu Leu Gln Thr Lys Ile Thr
            20                  25                  30

Asp

<210> SEQ ID NO 3
<211> LENGTH: 33
<212> TYPE: PRT
<213> ORGANISM: Artificial Sequence
<220> FEATURE:
<223> OTHER INFORMATION: Peptide GL-0001

<400> SEQUENCE: 3

His Gly Glu Gly Ser Phe Gly Ser Asp Met Ser Ile Ala Leu Asp Lys
1               5                   10                  15

Leu Ala Ala Arg Asp Phe Val Asn Trp Leu Leu Gln Thr Lys Ile Thr
            20                  25                  30

Asp

<210> SEQ ID NO 4
<211> LENGTH: 30
<212> TYPE: PRT
<213> ORGANISM: Artificial Sequence
<220> FEATURE:
<223> OTHER INFORMATION: Peptide GL-0007
<220> FEATURE:
<221> NAME/KEY: MOD_RES
<222> LOCATION: (30)..(30)
<223> OTHER INFORMATION: AMIDATION

<400> SEQUENCE: 4
```

```
His Gly Glu Gly Ser Phe Gly Ser Asp Phe Ser Ile Ala Leu Asp Lys
1               5                   10                  15

Leu Ala Ala Arg Asp Phe Val Asn Trp Leu Leu Gln Thr Lys
            20                  25                  30
```

<210> SEQ ID NO 5
<211> LENGTH: 42
<212> TYPE: PRT
<213> ORGANISM: Artificial Sequence
<220> FEATURE:
<223> OTHER INFORMATION: Peptide GL-0001-Tag

<400> SEQUENCE: 5

```
His Gly Glu Gly Ser Phe Gly Ser Asp Met Ser Ile Ala Leu Asp Lys
1               5                   10                  15

Leu Ala Ala Arg Asp Phe Val Asn Trp Leu Leu Gln Thr Lys Ile Thr
            20                  25                  30

Asp Gly Ala Ala Asp Asp Asp Asp Asp
        35                  40
```

<210> SEQ ID NO 6
<211> LENGTH: 30
<212> TYPE: PRT
<213> ORGANISM: Artificial Sequence
<220> FEATURE:
<223> OTHER INFORMATION: Peptide GL-0002
<220> FEATURE:
<221> NAME/KEY: MOD_RES
<222> LOCATION: (30)..(30)
<223> OTHER INFORMATION: AMIDATION

<400> SEQUENCE: 6

```
His Gly Glu Gly Ser Phe Val Ser Asp Met Ser Ile Val Leu Asp Lys
1               5                   10                  15

Leu Ala Ala Arg Asp Phe Val Asn Trp Leu Leu Gln Thr Lys
            20                  25                  30
```

<210> SEQ ID NO 7
<211> LENGTH: 30
<212> TYPE: PRT
<213> ORGANISM: Artificial Sequence
<220> FEATURE:
<223> OTHER INFORMATION: Peptide GL-0003
<220> FEATURE:
<221> NAME/KEY: MOD_RES
<222> LOCATION: (30)..(30)
<223> OTHER INFORMATION: AMIDATION

<400> SEQUENCE: 7

```
His Gly Glu Gly Ser Phe Val Ser Glu Met Ser Ile Val Leu Asp Lys
1               5                   10                  15

Leu Ala Ala Arg Asp Phe Val Asn Trp Leu Leu Gln Thr Lys
            20                  25                  30
```

<210> SEQ ID NO 8
<211> LENGTH: 30
<212> TYPE: PRT
<213> ORGANISM: Artificial Sequence
<220> FEATURE:
<223> OTHER INFORMATION: Peptide GL-0004
<220> FEATURE:
<221> NAME/KEY: MOD_RES
<222> LOCATION: (30)..(30)
<223> OTHER INFORMATION: AMIDATION

<400> SEQUENCE: 8

```
His Gly Glu Gly Ser Phe Val Ser Asp Met Ser Val Val Leu Asp Lys
1               5                   10                  15

Leu Ala Ala Arg Asp Phe Val Asn Trp Leu Leu Gln Thr Lys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Peptide GL-0005
<220> FEATURE:
<221> NAME/KEY: MOD_RES
<222> LOCATION: (30)..(30)
<223> OTHER INFORMATION: AMIDATION

<400> SEQUENCE: 9

His Gly Glu Gly Ser Phe Val Ser Asp Leu Ser Val Val Leu Asp Lys
1               5                   10                  15

Leu Ala Ala Arg Asp Phe Val Asn Trp Leu Leu Gln Thr Lys
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Peptide GL-0006
<220> FEATURE:
<221> NAME/KEY: MOD_RES
<222> LOCATION: (30)..(30)
<223> OTHER INFORMATION: AMIDATION

<400> SEQUENCE: 10

His Gly Glu Gly Ser Phe Val Ser Asp Phe Ser Val Val Leu Asp Lys
1               5                   10                  15

Leu Ala Ala Arg Asp Phe Val Asn Trp Leu Leu Gln Thr Lys
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Peptide GL-0008
<220> FEATURE:
<221> NAME/KEY: MOD_RES
<222> LOCATION: (30)..(30)
<223> OTHER INFORMATION: AMIDATION

<400> SEQUENCE: 11

His Gly Glu Gly Ser Phe Thr Ser Asp Phe Ser Ile Ala Leu Asp Lys
1               5                   10                  15

Leu Ala Ala Arg Asp Phe Val Asn Trp Leu Leu Gln Thr Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Peptide GL-0009
<220> FEATURE:
<221> NAME/KEY: MOD_RES
<222> LOCATION: (30)..(30)
<223> OTHER INFORMATION: AMIDATION

<400> SEQUENCE: 12
```

```
His Gly Glu Gly Ser Phe Val Ser Asp Phe Ser Ile Ala Leu Asp Lys
1               5                   10                  15

Leu Ala Ala Arg Asp Phe Val Asn Trp Leu Leu Gln Thr Lys
            20                  25                  30

<210> SEQ ID NO 13
<211> LENGTH: 9
<212> TYPE: PRT
<213> ORGANISM: Artificial Sequence
<220> FEATURE:
<223> OTHER INFORMATION: Peptide tag

<400> SEQUENCE: 13

Gly Ala Ala Asp Asp Asp Asp Asp Asp
1               5

<210> SEQ ID NO 14
<211> LENGTH: 33
<212> TYPE: PRT
<213> ORGANISM: Artificial Sequence
<220> FEATURE:
<223> OTHER INFORMATION: Peptide Co-3 of WO2018/069442

<400> SEQUENCE: 14

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 15
<211> LENGTH: 33
<212> TYPE: PRT
<213> ORGANISM: Artificial Sequence
<220> FEATURE:
<223> OTHER INFORMATION: Peptide Co-7 of WO2018/069442

<400> SEQUENCE: 15

His Ala Glu Gly Thr Phe Ile Ser Asp Tyr Ser Ile Ala Met Asp Lys
1               5                   10                  15

Leu Ala Ala Arg Asp Phe Ile Asn Trp Leu Ile Gln Thr Lys Ile Thr
            20                  25                  30

Asp

<210> SEQ ID NO 16
<211> LENGTH: 33
<212> TYPE: PRT
<213> ORGANISM: Artificial Sequence
<220> FEATURE:
<223> OTHER INFORMATION: Peptide Co-19 of WO2018/069442

<400> SEQUENCE: 16

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Gly Lys
            20                  25                  30

Lys
```